US011857790B2

(12) United States Patent
Molina et al.

(10) Patent No.: US 11,857,790 B2
(45) Date of Patent: *Jan. 2, 2024

(54) ELECTRICAL STIMULATION MODULATION

(71) Applicant: Medtronic, Inc., Minneapolis, MN (US)

(72) Inventors: Rene A Molina, Maple Grove, MN (US); Robert S. Raike, Minneapolis, MN (US); Scott R. Stanslaski, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/652,836

(22) Filed: Feb. 28, 2022

(65) Prior Publication Data
US 2022/0249846 A1   Aug. 11, 2022

Related U.S. Application Data

(63) Continuation of application No. 16/752,224, filed on Jan. 24, 2020, now Pat. No. 11,260,231.

(51) Int. Cl.
*A61N 1/05* (2006.01)
*A61N 1/36* (2006.01)

(52) U.S. Cl.
CPC ....... *A61N 1/36092* (2013.01); *A61N 1/0534* (2013.01); *A61N 1/36196* (2013.01)

(58) Field of Classification Search
CPC .............. A61N 1/36092; A61N 1/0534; A61N 1/36196; A61N 1/36067; A61N 1/36132; A61N 1/36139; A61N 1/36171
See application file for complete search history.

(56) References Cited

U.S. PATENT DOCUMENTS 7,483,747 B2   1/2009   Gliner et al.
7,715,910 B2   5/2010   Hargrove et al.
(Continued)

FOREIGN PATENT DOCUMENTS

WO   2004/093981 A1   11/2004

OTHER PUBLICATIONS

International Preliminary Report on Patentability from International Application No. PCT/US2021/014185 dated Aug. 4, 2022, 8 pp.
(Continued)

*Primary Examiner* — Ankit D Tejani
*Assistant Examiner* — Joshua Brendon Solomon
(74) *Attorney, Agent, or Firm* — Shumaker & Sieffert, P.A.

(57) ABSTRACT

Techniques, systems, and devices are disclosed for delivering stimulation therapy to a patient. In one example, a medical device determines a first set of stimulation parameters that define entrainment stimulation pulses configured to entrain electrical activity in a patient. The medical device may control a stimulation generator to generate the entrainment stimulation pulses according to the first set of stimulation parameters. The medical device may further determine a second set of stimulation parameters that define at least one desynchronization stimulation pulse configured to disrupt at least a portion of the electrical activity entrained by the entrainment stimulation pulses. The medical device may subsequently control the stimulation generator to generate the desynchronization stimulation pulse(s) according to the second set of stimulation parameters.

22 Claims, 15 Drawing Sheets

(56) References Cited

U.S. PATENT DOCUMENTS

| | | |
|---|---|---|
| 8,463,378 B2 | 6/2013 | Tass |
| 8,718,780 B2 | 5/2014 | Lee |
| 9,138,582 B2 | 9/2015 | Doan et al. |
| 9,592,384 B2 | 3/2017 | Tass |
| 9,694,183 B2 | 7/2017 | Grandhe |
| 9,737,711 B2 | 8/2017 | Twyford et al. |
| 10,065,464 B2 | 9/2018 | Grill et al. |
| 10,118,040 B2 | 11/2018 | Zhu |
| 10,207,109 B2 | 2/2019 | Zhu et al. |
| 10,406,368 B2 | 9/2019 | Hershey et al. |
| 11,260,231 B2 | 3/2022 | Molina et al. |
| 2006/0015153 A1 | 1/2006 | Gliner et al. |
| 2008/0103548 A1 | 5/2008 | Fowler et al. |
| 2009/0082691 A1 | 3/2009 | Denison et al. |
| 2011/0196446 A1 | 8/2011 | Wu et al. |
| 2011/0201977 A1 | 8/2011 | Tass |
| 2012/0277820 A1 | 11/2012 | Wu et al. |
| 2014/0277281 A1 | 9/2014 | Grandhe |
| 2016/0022168 A1 | 1/2016 | Luczak et al. |
| 2016/0106981 A1 | 4/2016 | Twyford et al. |
| 2017/0128729 A1 | 5/2017 | Netoff et al. |
| 2017/0216602 A1 | 8/2017 | Waataja et al. |
| 2017/0296823 A1 | 10/2017 | Hershey et al. |
| 2018/0085586 A1 | 3/2018 | Stanslaski et al. |
| 2018/0193653 A1 | 7/2018 | Bokil |
| 2019/0022394 A1 | 1/2019 | Fayram et al. |
| 2019/0030339 A1 | 1/2019 | Baru et al. |
| 2019/0290912 A1 | 9/2019 | Raike et al. |

OTHER PUBLICATIONS

Holt et al., "Phasic Burst Stimulation: A Closed-Loop Approach to Tuning Deep Brain Stimulation Parameters for Parkinson's Disease," PLoS Computational Biology, 12.7: e1005011, Jul. 14, 2016, 10pp.

International Search Report and Written Opinion of International Application No. PCT/US2021/014185, dated Apr. 21, 2021, 13 pp.

Prosecution History from U.S. Appl. No. 16/752,224, now issued U.S. Pat. No. 11,260,231, dated May 14, 2021 through Oct. 21, 2021, 42 pp.

ELECTRICAL STIMULATION MODULATION

This application is a continuation of U.S. patent application Ser. No. 16/752,224, filed Jan. 24, 2020, the entire contents of which is incorporated herein by reference.

TECHNICAL FIELD

The disclosure relates to medical devices and, more particularly, to medical devices that deliver electrical stimulation therapy.

BACKGROUND

Medical devices may be used to treat a variety of medical conditions. Medical electrical stimulation devices, for example, may deliver electrical stimulation therapy to a patient via electrodes, such as implanted electrodes. Electrical stimulation therapy may include stimulation of nerve, muscle, or brain tissue, or other tissue within a patient. In some instances, an electrical stimulation device may be fully implanted within the patient. An electrical stimulation device may include an electrical stimulation generator and, in some examples, one or more implantable leads carrying electrodes. Alternatively, the electrical stimulation device may comprise a leadless stimulator. In some cases, implantable electrodes may be coupled to an external electrical stimulation device via one or more percutaneous leads or fully implanted leads.

In one example, patients afflicted with movement disorders or other neurodegenerative impairment, whether by disease or trauma, may experience muscle control and movement problems, such as rigidity, bradykinesia (i.e., slow physical movement), rhythmic hyperkinesia (e.g., tremor), nonrhythmic hyperkinesia (e.g., tics) or akinesia (i.e., a loss of physical movement). Delivery of electrical stimulation and/or a fluid (e.g., a pharmaceutical drug) by a medical device to one or more sites, such as a brain, spinal cord, leg muscle or arm muscle, in a patient may help alleviate, and in some cases, eliminate symptoms associated with such disorders, among other example disorders. In such examples, the electrical stimulation device may deliver electrical stimulation pulses to targeted areas of a patient, such as the brain of the patient or particular regions of the brain, in order to help alleviate or eliminate symptoms of various disorders, including movement disorders.

SUMMARY

In general, the disclosed technology relates to systems, devices, and techniques for delivering electrical stimulation via a medical device to a patient, such as to the brain of the patient. The processing circuitry of a medical device may modulate the delivery of electrical stimulation in order to alter bioelectrical signals of the patient. For example, the modulation of electrical stimulation pulses may be configured to change bioelectrical signals of the brain to exhibit a desired behavior and/or cease an undesired behavior. The processing circuitry may achieve such modulation by controlling a stimulation generator to generate and deliver, to one or more electrodes, entrainment stimulation pulses in order to entrain electrical activity in the patient, followed by desynchronization stimulation pulse(s) (e.g., therapeutic stimulation pulse(s)) configured to disrupt electrical activity entrained by the entrainment stimulation pulses. In this way, the stimulation generator may alternate between a priming phase that entrains electrical signals of the brain and a desynchronization phase that desynchronizes electrical signals in at least a portion of the brain. Such phases may or may not overlap with one another in order to provide optimal therapeutic effect. Furthermore, the processing circuitry may adjust one or both of the phases over time in order to provide therapy tailored for the patient based on one or more detected physiological signals from the patient.

In one example, the disclosure is directed to a system comprising: a stimulation generator configured to generate stimulation pulses deliverable via at least one electrical lead comprising at least one electrode, and processing circuitry configured to: determine a first set of stimulation parameters that define entrainment stimulation pulses configured to entrain electrical activity in a brain of a patient; control the stimulation generator to generate the entrainment stimulation pulses according to the first set of stimulation parameters; determine a second set of stimulation parameters that define at least one desynchronization stimulation pulse configured to disrupt at least a portion of electrical activity entrained by the entrainment stimulation pulses, the second set of stimulation parameters being different from the first set of stimulation parameters; and subsequent to generating the entrainment stimulation pulses, control the stimulation generator to generate the at least one desynchronization stimulation pulse according to the second plurality of stimulation parameters.

In another example, the disclosure is directed to a method that includes: determining a first set of stimulation parameters that define entrainment stimulation pulses configured to entrain electrical activity in a brain of a patient; controlling a stimulation generator to generate the entrainment stimulation pulses according to the first set of stimulation parameters; determining a second set of stimulation parameters that define at least one desynchronization stimulation pulse configured to disrupt at least a portion of electrical activity of the brain entrained by the entrainment stimulation pulses, the second set of stimulation parameters being different from the first set of stimulation parameters; and subsequent to generating the entrainment stimulation pulses, controlling the stimulation generator to generate the at least one desynchronization stimulation pulse according to the second set of stimulation parameters.

In yet another example, a non-transitory computer-readable storage medium having stored thereon instructions that, when executed, cause one or more processors to at least: determine a first set of stimulation parameters that define entrainment stimulation pulses configured to entrain electrical activity in a brain of a patient; control a stimulation generator to generate the entrainment stimulation pulses according to the first set of stimulation parameters; determine a second set of stimulation parameters that define at least one desynchronization stimulation pulse configured to disrupt at least a portion of electrical activity of the brain entrained by the entrainment stimulation pulses, the second set of stimulation parameters being different from the first set of stimulation parameters; and subsequent to generating the entrainment stimulation pulses, control the stimulation generator to generate the at least one desynchronization stimulation pulse according to the second set of stimulation parameters.

In another example, the disclosure is directed to a system, the system including: means for determining a first set of stimulation parameters that define entrainment stimulation pulses configured to entrain electrical activity in a brain of a patient; means for controlling a stimulation generator to generate the entrainment stimulation pulses according to the first set of stimulation parameters; means for determining a second set of stimulation parameters that define at least one desynchronization stimulation pulse configured to disrupt at least a portion of electrical activity of the brain entrained by the entrainment stimulation pulses the second set of stimulation parameters being different from the first set of stimulation parameters; and means for controlling the stimulation generator to generate the at least one desynchronization stimulation pulse according to the second set of stimulation parameters.

The details of one or more aspects of the disclosure are set forth in the accompanying drawings and the description below. Other features, objects, and advantages will be apparent from the description and drawings, and from the claims.

BRIEF DESCRIPTION OF THE DRAWINGS

Like reference characters refer to like elements throughout the figures and description.

DETAILED DESCRIPTION

Figure 1:
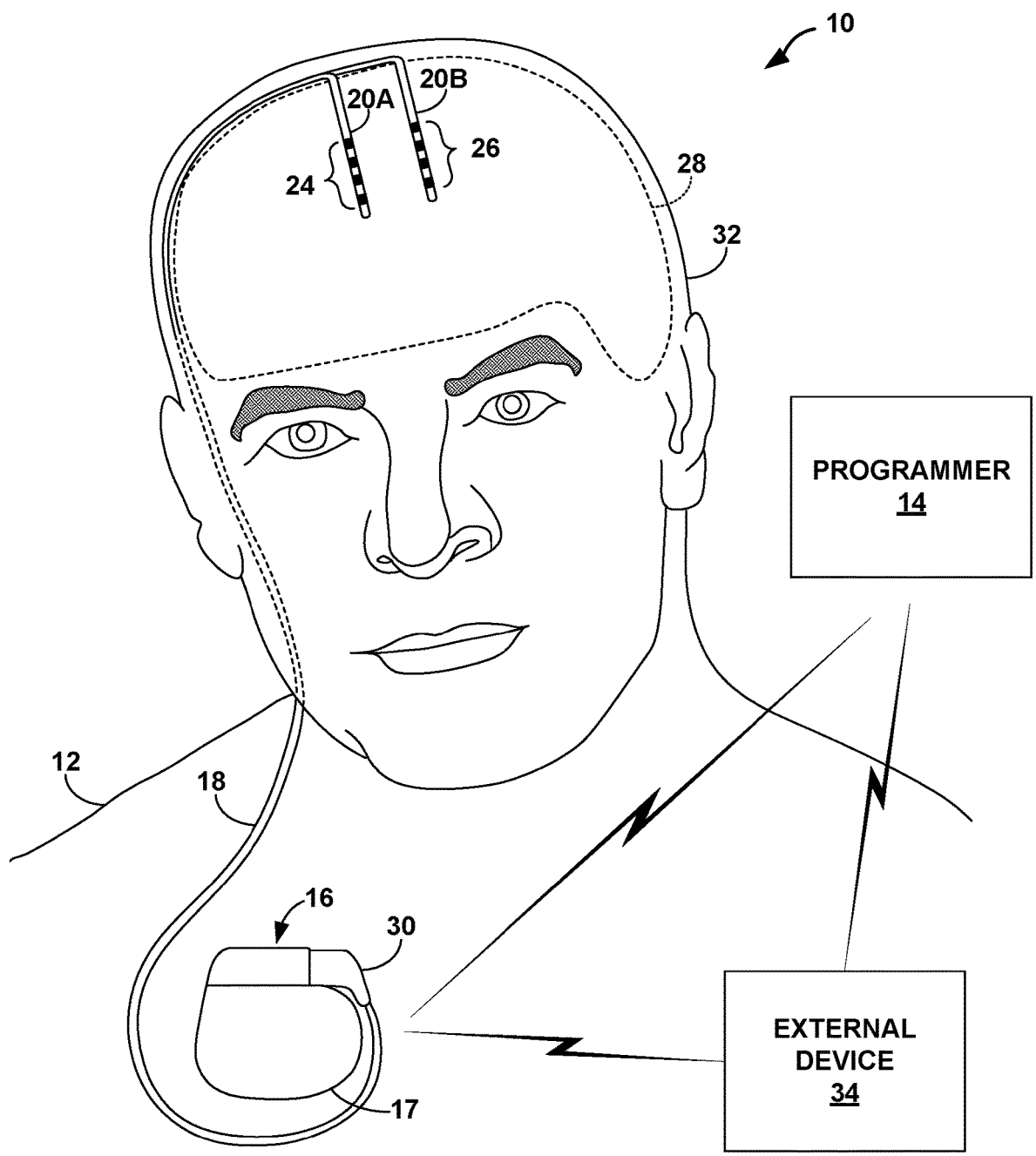
FIG. 1 is a conceptual diagram illustrating an example electrical stimulation system.

Systems, devices, and techniques for modulating electrical stimulation delivered to a patient are described. Specifically, a stimulation generator may generate and deliver via a medical lead, different phases of electrical stimulation to a patient. Such stimulation may be directed to certain regions of the brain of the patient during Deep Brain Stimulation (DBS), but similar stimulation may also be delivered as spinal cord stimulation (SCS), pelvic stimulation, peripheral nerve stimulation, muscle stimulation, etc., in other examples.

In general, DB S therapy may involve monolithic electrical therapy that follows preset stimulation parameters, such as preset frequencies, amplitudes, or pulse width parameters. In this manner, a single pulse frequency, pulse width, and amplitude may define pulses delivered in an open loop configuration. Such electrical stimulation, however, may not provide therapy in an efficient manner, for example, because the delivery of such electrical stimulation is often applied indiscriminately to certain regions of the brain and without considering patient specific conditions, conservation of electrical power, stimulation time, etc. before achieving a sought after therapeutic result. In addition, such electrical stimulation may take longer to achieve a therapeutic result if the electrical activity of the brain does not have uniform or known parameters. As such, the electrical stimulation may be less effective for the patient, consume more electrical power, or otherwise reduce overall system performance in treating the patient. In other examples, electrical stimulators may use bursts of electrical energy (e.g., bursts of pulses) in an effort to influence electrical activity into exhibiting a particular behavior. Such bursts of electrical stimulation, however, may be applied indiscriminately in such a way that the electrical stimulation therapy may not effectively decouple and target smaller, more local activation regions within an entrained volume during brief sessions of electrical stimulation. In this way, such electrical stimulation may also consume extraneous electrical power in the process of providing therapy.

The aforementioned issues, among others, may be addressed by the disclosed electrical stimulation modulation techniques by delivering entrainment stimulation pulses (e.g., priming phase pulses), followed by, or in parallel with, one or more desynchronization stimulation pulse(s) (e.g., a set of desynchronization phase pulses). Specifically, the stimulation generator may alternate between entrainment stimulation pulses configured to place at least a portion of the brain into a known electrical state and desynchronization stimulation pulses configured to disrupt at least a portion of the entrained electrical activity.

In an example involving DBS, the stimulation generator may generate and deliver electrical stimulation therapy that includes delivery of priming phase pulses delivered at a first frequency and delivery of desynchronization phase pulse(s) delivered at a second frequency. In such examples, the entrainment stimulation pulses delivered by the stimulation generator may first cause entrainment of a volume of electrical activity, such as neuronal activity, using entrainment stimulation parameters. Subsequently, the stimulation generate may generate and deliver the desynchronization pulse (s) to target specific portions (e.g., neuronal subpopulations or a smaller volume) of the entrained population of neurons.

Generally, entrainment occurs when the frequency of a bioelectrical signal aligns with an input frequency, such as the input frequency of electrical stimulation or of another stimuli (e.g., audible stimuli, etc.). For example, entrained bioelectrical signals may align with a temporal structure of the input stimuli. For example, the entrained bioelectrical signals may begin to transmit at a rhythm or frequency that matches or is approximately equal to a rhythm or frequency of the input stimuli. In another example of alignment, the entrained bioelectrical signals may synchronize with the input stimuli, such that the entrained bioelectrical signals transmit at a rhythm or frequency that is synchrony with the input stimuli without necessarily matching or equaling the rhythm or frequency of the input stimuli. For example, the entrained bioelectrical signals may transmit out of phase with the input stimuli or at a different rate while aligning or maintaining alignment with a temporal structure of the input stimuli (e.g., frequency, rhythm, etc.).

In the case of electrical stimulation, entrainment of bioelectrical signals, such as those in the brain, may occur when the waveform frequency of a bioelectrical signal aligns, or at least begins to align, with the frequency oscillation of the electrical stimulation. That is, entrainment generally refers to the phase alignment of brain oscillations with an external stimuli. In some instances, the entrainment stimulation pulses may also provide therapy to the patient, such as alpha, delta, theta, beta, and/or gamma entrainment therapy, whereas in other examples, the entrainment stimulation pulses are not configured to provide therapy. In any case, the entrainment stimulation pulses are delivered according to parameters configured to at least entrain electrical activity (e.g., neuronal activity, cellular activity, etc.) in the patient.

The stimulation generator may then generate and deliver desynchronization stimulation pulse(s) according to a set of stimulation parameters that is at least partially different from the set of stimulation parameters that defines the entrainment stimulation pulses (e.g., at least one of a different frequency, different electrode configuration, different amplitude, different pulse width, etc.). For example, the frequency of the desynchronization stimulation pulse(s) may be higher than that of the frequency of the entrainment stimulation pulses that entrained the electrical activity in the patient. In addition, or alternatively, the amplitude of the desynchronization stimulation pulse(s) may be lower than the amplitude of the entrainment stimulation pulses. As such, the electrical stimulation of the desynchronization pulse(s) may be configured to recruit a smaller and/or more local volume of activation (VOA) relative to a VOA of the entrained electrical activity. In this way, the stimulation generator may provide therapeutic pulses configured to disrupt specific portions of the entrained electrical activity. This disruption of the entrained electrical activity may promote a reduction of symptoms related to movement disorders, such as a reduction in tremor.

In some examples, the stimulation generator may generate and deliver the desynchronization stimulation pulse(s) to one or more of the same electrodes selected to deliver the entrainment stimulation. In another example, the stimulation generator may generate and deliver the desynchronization stimulation pulse(s) to one or more different electrodes, or in some instances, to only some of the same electrodes used to deliver the entrainment stimulation, along with a different combination of electrodes as well. The desynchronization stimulation pulse(s) may be used to disrupt the electrical activity entrained by the entrainment stimulation pulses, or at least a portion of the entrained electrical activity, in order to provide therapy to the patient, such as for a patient suffering from a neurological disorders (e.g., Parkinson's disease, essential tremor, epilepsy, etc.). For example, the desynchronization stimulation pulse(s) may be used to destructively interfere with the entrained electrical activity. In any case, providing electrical stimulation in accordance with the various techniques of this disclosure, may allow a medical device to provide improved electrical stimulation therapy by first entraining the electrical activity and then disrupting the entrained activity for therapeutic purposes, such as to destroy patient-specific network synchrony and/or to allow for the natural evolution of neuro-population resynchronization to occur. For example, the stimulation generator may provide desynchronization pulse(s) that cause a local neuronal region to spatiotemporally decouple from a larger network recruited through delivery of the entrainment stimulation pulses, at which point, the stimulation generator may continue to provide patient-tailored desynchronization pulse(s) and/or entrainment pulses throughout the duration of a given therapy session.

In some examples, stimulation parameters for either the entrainment stimulation pulses and/or the desynchronization stimulation pulse(s) may be based on patient-specific biomarkers, such as measured frequencies in the local field potential (LFP) of the patient associated with symptoms (e.g., tremor), electrophysiological markers, physical patient movement sensors (e.g., one or more accelerometers), other electrical brain signals, etc. These biomarkers may thus be indicative of features, characteristics, or other aspects of a physiological signal sensed by one or more devices. In some instances, the physiological signals and/or patient-specific biomarkers may be received from an external device, such as a wearable device. For example, processing circuitry, such as that of the stimulation generator, may determine stimulation parameters for the stimulation pulses from sensed physiological signals, biomarkers of the patient, and/or from the specifically targeted region of the patient. The processing circuitry may then adjust one or more stimulation parameters (e.g., adjust a value of one or more respective stimulation parameters) accordingly to deliver the stimulation pulse(s). The stimulation generator may use the biomarkers to establish initial stimulation parameters with which stimulation can proceed in an open loop configuration. The processing circuitry of the stimulation generator may tailor the alternating pulse pattern (e.g., pulse frequency and/or duration), and transitions between pulse patterns, based on the patient-specific biomarkers, but the processing circuitry may not necessarily modulate those parameters during stimulation based on the biomarkers or any other feedback indicating efficacy of the stimulation.

In some examples, the stimulation generator may interleave a rest phase between the entrainment stimulation pulses and the desynchronization pulses. In such examples, parameters for the rest phase (e.g., duration of the rest phase) may also be based on one or more biomarkers of the patient.

In a closed loop configuration, the system may additionally or alternatively tailor at least one stimulation parameter that at least partially defines the entrainment stimulation pulses, desynchronization stimulation pulses, and/or any other aspect of the pattern of pulses based on one or more biomarkers and/or feedback received regarding the efficacy of the stimulation pulses. The biomarkers may be associated with brain signals, movement sensors, or any other physiological signal. As another example, the feedback may be based on an indication as to the effectiveness of the desynchronization pulses in activating specific regions of the brain or decoupling specific VOAs from the entrained VOA. Feedback may be achieved through the use of a stimulation lead that is also capable of providing sensing capabilities.

In some examples, electrical stimulation may be delivered by a medical device to the brain of the patient to manage or otherwise treat one or more symptoms of a patient disorder. The brain of the patient may exhibit brain signals across a broad frequency spectrum. However, in some examples, oscillation of bioelectrical brain signals at a particular frequency or in a frequency band or range may be associated with one or more symptoms or brain states of a patient disorder. An example brain state may include a sleep state of a patient. For example, bioelectrical brain signals oscillating in a particular frequency range may be associated with one or more symptoms of a patient disorder in the sense that such symptoms frequently occur or manifest themselves when the bioelectrical brain signals oscillate at such a frequency range. Such occurrences may be a result of the brain signal oscillations within one or more regions of the brain of a patient interfering with the normal function of that region of the brain. As used herein, a frequency or range of frequencies may be referred to as a pathological frequency or pathological frequency range when oscillations of brain signals at such frequency or frequencies are associated in such a manner with one or more symptoms of a patient disorder. Similarly, bioelectrical brain signals oscillating at one or more pathological frequencies may be referred to as pathological brain signals.

As one example, in the case of Parkinson's disease, beta frequency oscillations (e.g., between approximately 13 Hertz to approximately 30 Hertz) in the subthalamic nucleus (STN), globus pallidus interna (GPi), globus pallidus externa (GPe), and/or other areas of the basal ganglia may be associated with one or more motor symptoms including, e.g., rigidity, akinesia, bradykinesia, dyskinesia, and/or resting tremor. In the case of epilepsy, beta frequency oscillations may occur within one or more sites within the Circuit of Papez, including, e.g., anterior nucleus, internal capsule, cingulate, entorhinal cortex, hippocampus, fornix, mammillary bodies, or mammillothalamic tract (MMT). These motor symptoms may be associated with bioelectrical brain signals oscillating in the beta frequency range in the sense that such symptoms frequently occur when the bioelectrical brain signals oscillate within the beta frequency range. For example, persistence of high amplitude, long duration oscillation in the beta frequency range may result in oscillatory "interference" with normal low amplitude, short duration beta oscillations within the brain. Such interference may limit the normal functions of the above-mentioned regions of the brain. The high amplitude, long duration oscillations of the bioelectrical brain signals may be at a lower frequency than other higher frequency intrinsic signals within the bioelectrical brain signals.

Networks of oscillating signals in neurons may be synchronized by electrical and chemical signals that cause the activity of the network to phase lock and resonate at some frequency. In some examples, the symptoms of Parkinson's disease or epilepsy may generally manifest themselves in conjunction with the presence of high amplitude, long duration beta frequency range oscillations. In some examples, the frequency of symptom manifestations may increase in conjunction with the presence of high amplitude, long duration beta frequency range oscillations. In further examples, gamma oscillations (e.g., oscillations comprising a frequency of about 35 Hertz to 200 Hertz) may occur in the hippocampus. Such gamma oscillations may also be associated with one or more symptoms of a patient disorder. In further examples, other high frequency oscillations comprising a frequency within a range of 100 Hertz to 500 Hertz may be associated with one or more symptoms of a patient disorder. As described herein, the desynchronization stimulation pulses delivered with different pulse frequency, pulse width, and/or amplitude may disrupt the entrained electrical signal and the oscillations associated with patient symptoms.

FIG. 1 is a conceptual diagram illustrating an example therapy system 10 in accordance with examples of the disclosure. In FIG. 1, example therapy system 10 may deliver electrical stimulation therapy to treat or otherwise manage a patient condition, such as, e.g., a movement disorder of patient 12. One example of a movement disorder treated by the delivery of DBS via system 10 may include Parkinson's disease or epilepsy. Patient 12 ordinarily will be a human patient. In some cases, however, therapy system 10 may be applied to other mammalian or non-mammalian non-human patients.

For ease of illustration, examples of the disclosure will primarily be described with regard to the treatment of movement disorders and, in particular, the treatment of Parkinson's disease, e.g., by reducing or preventing the manifestation of symptoms exhibited by patients suffering from Parkinson's disease. As noted above, such symptoms may include rigidity, akinesia, bradykinesia, dyskinesia, and/or resting tremor. However, the treatment of one or more patient disorders other than that of Parkinson's disease by employing the techniques described herein is contemplated. For example, the described techniques may be employed to manage or otherwise treat symptoms of other patient disorders, such as, but not limited to, epilepsy, psychological disorders, mood disorders, seizure disorders or other neurogenerative impairment. In one example, such techniques may be employed to provide therapy to patient to manage Alzheimer's disease.

Therapy system 10 includes medical device programmer 14, implantable medical device (IMD) 16, lead extension 18, and one or more leads 20A and 20B (collectively "leads 20") with respective sets of electrodes 24, 26. IMD 16 includes stimulation therapy circuitry that includes a stimulation generator that generates and delivers electrical stimulation therapy to one or more regions of brain 28 of patient 12 via a subset of electrodes 24, 26 of leads 20A and 20B, respectively. In the example shown in FIG. 1, therapy system 10 may be referred to as a deep brain stimulation (DBS) system because IMD 16 provides electrical stimulation therapy directly to tissue within brain 28, e.g., a tissue site under the dura mater of brain 28. In other examples, leads 20 may be positioned to deliver therapy to a surface of brain 28 (e.g., the cortical surface of brain 28).

In some examples, delivery of stimulation to one or more regions of brain 28, such as an anterior nucleus (AN), thalamus or cortex of brain 28, provides an effective treatment to manage a disorder of patient 12. In some examples, IMD 16 may provide cortical stimulation therapy to patient 12, e.g., by delivering electrical stimulation to one or more tissue sites in the cortex of brain 28. In cases in which IMD 16 delivers electrical stimulation to brain 28 to treat Parkinson's disease by disrupting entrained brain signals, target stimulation sites may include one or more basal ganglia sites, including, e.g., subthalamic nucleus (STN), globus pallidus interna (GPi), globus pallidus externa (GPe), pedunculopontine nucleus (PPN), thalamus, substantia nigra pars reticulata (SNr), internal capsule, and/or motor cortex. In cases in which IMD 16 delivers electrical stimulation to brain 28 to treat epilepsy by disrupting entrained brain signals, target stimulation sites may include one or more sites within the Circuit of Papez, including, e.g., anterior nucleus, internal capsule, cingulate, entorhinal cortex, hippocampus, fornix, mammillary bodies, or MMT. Brain signals with oscillations in the beta frequency range may be considered pathological brain signals. As will be described below, IMD 16 may deliver electrical stimulation pulses configured to entrain electrical activity and then disrupt the entrained electrical activity based on the frequency of the pathological brain signal. In an illustrative example involving a particular disease (e.g., Parkinson's disease), IMD 16 may entrain, via DBS, brain oscillations at 130 Hertz stimulation (e.g., F_stim). The entrained brain oscillation may be found in the STN and Cortex of patient 12. As such, the entrained brain oscillations in patient 12 may be observed in the STN and Cortex at half of the entrainment stimulation frequency (e.g., 65 Hertz in this particular example). In such instances, IMD 16 may then disrupt the entrained brain oscillations (e.g., the entrained oscillations comprising half of the F_stim) by delivering a set of desynchronization pulses as described herein.

In another example, the pathological frequency range is a beta frequency range of about 11 Hertz to about 35 Hertz. For examples in which IMD 16 senses the bioelectrical brain signals at one or more sites of brain 28 to receive feedback from the patient and/or tailor the stimulation pulses based on patient-specific biomarkers, the target stimulation site(s) for electrical stimulation delivered to brain 28 of patient 12 may be the same and/or different than the sensing site.

In the example shown in FIG. 1, IMD 16 may be implanted within a subcutaneous pocket above the clavicle of patient 12. In other examples, IMD 16 may be implanted within other regions of patient 12, such as a subcutaneous pocket in the abdomen or buttocks of patient 12 or proximate the cranium of patient 12. Implanted lead extension 18 is coupled to IMD 16 via connector block 30. In some examples, electrical contacts may electrically couple the electrodes 24, 26 carried by leads 20 to IMD 16. Lead extension 18 traverses from the implant site of IMD 16 and through the cranium of patient 12 to access brain 28. IMD 16 may comprise a hermetic housing 17 to substantially enclose components, such as a processing circuitry, sensing circuitry, memory, etc.

Leads 20A and 20B may be implanted within the right and left hemispheres, respectively, of brain 28 in order deliver electrical stimulation to one or more regions of brain 28, which may be selected based on many factors, such as the type of patient condition for which therapy system 10 is implemented to manage. Other implant sites for leads 20 and IMD 16 are contemplated. For example, IMD 16 may be implanted on or within cranium 32 or leads 20 may be implanted within the same hemisphere or IMD 16 may be coupled to a single lead that is implanted in one or both hemispheres of brain 28.

Leads 20 may be positioned to deliver electrical stimulation to one or more target tissue sites within brain 28 to manage patient symptoms associated with a disorder of patient 12. Leads 20 may be implanted to position electrodes 24, 26 at desired locations of brain 28 through respective holes in cranium 32. Leads 20 may be placed at any location within brain 28 such that electrodes 24, 26 are capable of providing electrical stimulation to target tissue sites within brain 28 during treatment. For example, in the case of Parkinson's disease, for example, leads 20 may be implanted to deliver electrical stimulation to one or more basal ganglia sites, including, e.g., subthalamic nucleus (STN), globus pallidus interna (GPi), globus pallidus externa (GPe), pedunculopontine nucleus (PPN), thalamus, substantia nigra pars reticulata (SNr), internal capsule, and/or motor cortex. As another example, in the case of epilepsy, for example, leads 20 may be implanted to deliver electrical stimulation to one or more sites within the Circuit of Papez, including, e.g., anterior nucleus, internal capsule, cingulate, entorhinal cortex, hippocampus, fornix, mammillary bodies, or MMT.

Although leads 20 are shown in FIG. 1 as being coupled to a common lead extension 18, in other examples, leads 20 may be coupled to IMD 16 via separate lead extensions or directly coupled to IMD 16. Moreover, although FIG. 1 illustrates system 10 as including two leads 20A and 20B coupled to IMD 16 via lead extension 18, in some examples, system 10 may include one lead or more than two leads.

Leads 20 may deliver electrical stimulation to treat any number of neurological disorders or diseases in addition to movement disorders, such as seizure disorders or psychiatric disorders. Examples of movement disorders include a reduction in muscle control, motion impairment or other movement problems, such as rigidity, bradykinesia, rhythmic hyperkinesia, nonrhythmic hyperkinesia, dystonia, tremor, and akinesia. Movement disorders may be associated with patient disease states, such as Parkinson's disease, Huntington's disease, or epilepsy. Examples of psychiatric disorders include MDD, bipolar disorder, anxiety disorders, posttraumatic stress disorder, dysthymic disorder, and OCD. As described above, while examples of the disclosure are primarily described with regard to treating Parkinson's disease, treatment of other patient disorders via delivery of electrical stimulation to patient 12 is contemplated.

Leads 20 may be implanted within a desired location of brain 28 via any suitable technique, such as through respective burr holes or through a common burr hole in the cranium 32 of patient 12. Leads 20 may be placed at any location within brain 28 such that electrodes 24, 26 of leads 20 are capable of providing electrical stimulation to targeted tissue during treatment. Electrical stimulation generated from the stimulation generator (not shown) of IMD 16 may help prevent the onset of events associated with the patient's disorder or mitigate symptoms of the disorder. For example, a first electrical stimulation pulse train delivered by IMD 16 to brain 28 may have a frequency (and/or other stimulation parameter values) configured to entrain electrical activity, whereas a second desynchronization electrical stimulation pulse or pulse train may have a frequency configured to disrupt the entrained bioelectrical brain signals.

In the examples shown in FIG. 1, electrodes 24, 26 of leads 20 are shown as ring electrodes. Ring electrodes may deliver an electrical field to any tissue adjacent to leads 20. In other examples, electrodes 24, 26 of leads 20 may have different configurations. For example, electrodes 24, 26 of leads 20 may have a complex electrode array geometry that is capable of producing shaped electrical fields. The complex electrode array geometry may include multiple electrodes (e.g., partial ring or segmented electrodes) around the perimeter of each lead 20, rather than a ring electrode. In this manner, electrical stimulation may be directed to a specific direction from leads 20 to enhance therapy efficacy, target specific pathological regions using the desynchronization pulse(s), and/or target specific regions for entrainment using the entrainment stimulation pulses.

In some examples, a lead may include one or more ring electrodes together with one or more rings of segmented electrodes. In addition, housing 17 of IMD 16 may include one or more stimulation and/or sensing electrodes. Furthermore, leads 20 may be paddle leads, spherical leads, cylindrical leads, bendable leads, or any other type of shape effective in treating patient 12.

IMD 16 may generate and/or deliver electrical stimulation therapy to brain 28 of patient 12 according to one or more stimulation parameters or parameter values that define entrainment stimulation pulses and one or more stimulation parameters or parameter values that define desynchronization stimulation pulse(s). Where IMD 16 delivers electrical stimulation in the form of electrical pulses, for example, the stimulation may be characterized by selected pulse parameters, such as pulse amplitude, pulse rate or frequency, pulse width, or number of pulses. Where IMD 16 delivers electrical stimulation in the form of a sinusoidal wave, for example, the stimulation may be characterized by selected sinusoidal parameters, such as amplitude or cycle frequency. In some examples as used herein, a "stimulation pulse" or pulse(s) may generally refer to either a digital signal that causes an analog waveform, such as the aforementioned sinusoidal wave, or may refer to electrical pulses, depending on the context. In some examples, when different electrodes are available for delivery of stimulation, the program may be further characterized by different electrode combinations, which can include selected electrodes and their respective polarities. The exact parameter values of the electrical stimulation may be specific for the particular target stimulation site (e.g., the region of the brain) involved, as well as the particular patient and patient condition.

In addition to delivering electrical stimulation to manage a disorder of patient 12, therapy system 10 monitors one or more bioelectrical brain signals of patient 12. For example, IMD 16 may include sensing circuitry that senses bioelectrical brain signals within one or more regions of brain 28. In the example shown in FIG. 1, the signals generated by electrodes 24, 26 are conducted to IMD 16 via conductors. As described in further detail below, in some examples, processing circuitry of IMD 16 may sense the bioelectrical signals within brain 28 of patient 12 and control generation or delivery of entrainment stimulation pulses and desynchronization pulse(s) to brain 28 via electrodes 24, 26.

In some examples, the sensing circuitry of IMD 16 may receive the bioelectrical signals from electrodes 24, 26 or other electrodes positioned to monitor brain signals of patient 12. Electrodes 24, 26 may also be used to deliver electrical stimulation to target sites within brain 28 as well as sense brain signals within brain 28. However, IMD 16 can also use separate sensing electrodes to sense the bioelectrical brain signals. In some examples, the sensing circuitry of IMD 16 may sense bioelectrical brain signals via one or more of the electrodes 24, 26 that are also used to deliver electrical stimulation to brain 28. In other examples, one or more of electrodes 24, 26 may be used to sense bioelectrical brain signals while one or more different electrodes 24, 26 may be used to deliver electrical stimulation. In another example, system 10 may include an external device 34, such as a wearable device (not shown) or external monitoring device, that receives patient-specific biomarkers, or in some cases, bioelectrical signals, from patient 12. External device 34 may then transmit biomarker information and/or bioelectrical signal information, via telemetry circuitry, to programmer 14, IMD 16, and/or an external server (not shown) for further processing. As such, IMD 16, external device 34, and programmer 14 may interface with an external server via a network connection in order to perform the various techniques of this disclosure. In any case, the external device may include a wearable device worn on the wrist or ankle of patient 12, a headpiece or earpiece worn on or proximate the head of patient 12, a portable or mobile device configured to obtain biomarkers, or other external sensor devices (e.g., a smart phone having a sensor), etc.

Depending on the particular stimulation electrodes and sense electrodes used by IMD 16, IMD 16 may monitor brain signals and deliver electrical stimulation toward the same region of brain 28 or different regions of brain 28. In some examples, the electrodes used to sense bioelectrical brain signals may be located on the same lead used to deliver electrical stimulation, while in other examples, the electrodes used to sense bioelectrical brain signals may be located on a different lead than the electrodes used to deliver electrical stimulation. In some examples, a brain signal of patient 12 may be monitored with external electrodes, e.g., scalp electrodes of external device 34. Moreover, in some examples, the sensing circuitry that senses bioelectrical brain signals of brain 28 (e.g., the sensing circuitry that generates an electrical signal indicative of the activity within brain 28) is in a physically separate housing from housing 17 of IMD 16. However, in the example shown in FIG. 1 and the example primarily referred to herein for ease of description, the various circuitry of IMD 16 are enclosed within a common outer housing 17.

The physiological signals (e.g., bioelectrical brain signals) monitored by IMD 16 may reflect changes in electrical current produced by the sum of electrical potential differences across brain tissue. Examples of the monitored bioelectrical brain signals include, but are not limited to, an electroencephalogram (EEG) signal, an electrocorticogram (ECoG) signal, a local field potential (LFP) sensed from within one or more regions of brain 28 of patient 12, action potentials from single cells within the patient's brain, and/or Microelectrode recording (MER) of single cells within brain 28 of patient 12. These example bioelectrical brain signals, among others signals, may be used to identify one or more biomarkers. For example, processing circuitry 40 may identify one or more biomarkers within a raw or, in some cases, a filtered bioelectrical signal, physiological signal, etc. The one or more biomarkers may then be used to determine parameters of the entrainment stimulation pulses and/or the desynchronization stimulation pulse(s). In one example, processing circuitry 40 may identify a frequency of a physiological signal as a biomarker indicative of a disease or other problem of patient 12. That is, biomarkers may include features or characteristics that processing circuitry, such as that of IMD 16, may identify from one or more physiological signals.

Programmer 14 wirelessly communicates with IMD 16 as needed to provide or retrieve electrical stimulation information. Programmer 14 is an external computing device that the user, e.g., the clinician and/or patient 12, may use to communicate with IMD 16. For example, programmer 14 may be a clinician programmer that the clinician uses to communicate with IMD 16 and program one or more electrical stimulation programs for IMD 16. In some examples, programmer 14 may be a patient programmer that allows patient 12 to select programs and/or view and modify electrical stimulation parameters.

Programmer 14 may be a hand-held computing device with a display viewable by the user and an interface for providing input to programmer 14 (i.e., a user input mechanism). For example, programmer 14 may include a display screen (e.g., a touch screen display) that presents information to the user. In addition, programmer 14 may include a touch screen, keypad, buttons, a peripheral pointing device or another input mechanism that allows the user to navigate through the user interface of programmer 14 and provide input. In some examples, programmer 14 may be configured to obtain physiological signals from patient 12 and identify one or more biomarkers from the physiological signal and for patient 12, similar to how IMD 16 may obtain physiological signals from patient 12 and identify one or more biomarkers from the physiological signal and for patient 12. In another example, programmer 14 or IMD 16 may be configured to receive biomarker information from an external device, such as from external device 34.

In other examples, programmer 14 may be a larger workstation or a separate application within another multi-function device, rather than a dedicated computing device. For example, the multi-function device may be a notebook computer, tablet computer, workstation, cellular phone, personal digital assistant or another computing device that may run an application that enables the computing device to operate as a programmer 14. A wireless adapter coupled to the computing device may enable communication between the computing device and IMD 16.

When programmer 14 is configured for use by the clinician, programmer 14 may be used to transmit initial programming information to IMD 16. This initial information may include hardware information, such as the type of leads 20, the arrangement of electrodes 24, 26 on leads 20, the position of leads 20 within brain 28, programs defining electrical stimulation parameter values, and any other information that may be useful for programming into IMD 16.

The clinician may also store programs within IMD 16 with the aid of programmer 14. During a programming session, the clinician may determine one or more electrical stimulation parameters that may provide efficacious therapy to patient 12 to address patient symptoms. For example, the clinician may select one or more electrode combinations to which entrainment stimulation pulses are delivered and/or one or more electrode combinations to which desynchronization stimulation pulse(s) are delivered. During the programming session, patient 12 may provide feedback to the clinician as to the efficacy of the specific electrical stimulation being evaluated. In other examples, the clinician may evaluate the efficacy based on one or more physiological parameters of patient 12, heart rate, respiratory rate, muscle activity, perfusion indices, LFP signals, EEG signals, ECoG signals, etc.

Programmer 14 may also provide an indication to patient 12 when electrical stimulation is being delivered, such as when entrainment stimulation pulses are being delivered and stimulation parameters corresponding to the entrainment stimulation pulses, when desynchronization stimulation pulse(s) are being delivered and stimulation parameters corresponding to the desynchronization stimulation pulse(s), and when neither are being delivered, such as during a rest phase. In some examples, programmer 14 may include an ability to toggle the electrical stimulation from a closed loop configuration to an open loop configuration, and vice versa.

Whether programmer 14 is configured for clinician or patient use, programmer 14 is configured to communicate to IMD 16 and, optionally, another device, via wireless communication. Programmer 14, for example, may communicate via wireless communication with IMD 16. Programmer 14 may also communicate with another programmer or external device via a wired or wireless connection using any of a variety of local wireless communication techniques, such as RF communication according to the 802.11 or Bluetooth® specification sets, infrared (IR) communication according to the IRDA specification set, or other standard or proprietary telemetry protocols. Programmer 14 may also communicate with other programming devices or external device 34 via exchange of removable media, such as magnetic or optical disks, memory cards or memory sticks. Further, programmer 14 may communicate with IMD 16 and another programmer via remote telemetry techniques known in the art, communicating via a local area network (LAN), wide area network (WAN), public switched telephone network (PSTN), or cellular telephone network, for example.

Therapy system 10 may be implemented to provide chronic stimulation therapy to patient 12 over the course of several months or years. However, system 10 may also be employed on a trial basis to evaluate therapy before committing to full implantation. If implemented temporarily, some components of system 10 may not be implanted within patient 12. For example, patient 12 may be fitted with an external medical device, such as a trial stimulator, rather than IMD 16. The external medical device may be coupled to percutaneous leads or to implanted leads via a percutaneous extension. If the trial stimulator indicates DBS system 10 provides effective treatment to patient 12, the clinician may implant a chronic stimulator within patient 12 for relatively long-term treatment.

In accordance with the techniques of the disclosure, IMD 16 senses, via electrodes 24, 26 disposed along leads 20, one or more bioelectrical brain signals of brain 28 of patient 12. In some examples, IMD 16 senses one or more oscillations of the bioelectrical brain signals oscillating at a frequency associated with a pathological disease. In some examples, the one or more oscillations are within a beta frequency range of about 11 Hertz to about 35 Hertz. In other examples, the one or more oscillations are within a Theta frequency band of about 4 Hertz to about 12 Hertz. In other examples, the one or more oscillations are within a gamma frequency band of between about 35 Hertz to about 200 Hertz. In some examples, the one or more oscillations are associated with one or more symptoms of Parkinson's disease, such as tremor, rigidity, or bradykinesia, etc. In some examples, the one or more oscillations are associated with one or more symptoms of another disease, such as dystonia, essential tremor, Tourette's syndrome, obsessive compulsive disorder, epilepsy, or depression.

In some examples, IMD 16 may perform a stimulation program that aims to initially prime a large neuronal circuit and then deliver local disruptive, therapeutic stimulation or interference. For example, IMD 16 may deliver an initial priming stimulation at frequencies, pulse width and amplitudes configured to entrain brain regions and recruit a network of the brain. For example, IMD 16 may deliver an initial priming stimulation configured to entrain the STN region of brain 28. In such examples, IMD 16 may recruit a brain network, such as the basal ganglia brain network.

IMD 16 may then deliver desynchronization pulse(s) (e.g., therapeutic pulse, desynchronization phase pulse train) at a different combination of frequency, amplitude, or pulse width, to recruit a small, more local neuronal volume in order to target the most effective volume with directionality. For example, segmented electrode leads 20 may be used to provide directionality for electrical field generation.

In some examples, in order for the desynchronization stimulation pulse(s) to cause destructive interference with the entrained electrical activity (e.g., entrained oscillations of the bioelectrical brain signals of brain 28), the desynchronization stimulation pulse(s) may be out of phase from the one or more entrained oscillations by a phase amount greater than 120 degrees and less than 240 degrees (e.g., such as about 180 degrees), or by a phase amount greater than $2\pi/3$ radians and less than $4\pi/3$ radians (e.g., such as about $\pi$ radians). Further, it is noted that delivering the desynchronization stimulation pulse(s) in phase with the one or more oscillations of the bioelectrical brain signals of brain 28 (e.g., a phase amount in a range from about 0 degrees to 120 degrees, a range from about 240 degrees to about 360 degrees, a range from about 0 radians to about $2\pi/3$ radians, or a range of about $4\pi/3$ radians to $2\pi$ radians) may cause constructive interference with the one or more oscillations and may be avoided, if the goal is to suppress pathologic oscillations, or may be favored if the goal is to promote desirable oscillations. In any case, constructive interference may, in some instances, constitute a form of disruption of entrained electrical activity.

In some examples, IMD 10 delivers electrical stimulation therapy comprising desynchronization pulse(s) selected based on biomarkers of patient 12. However, in other examples, instead of electrical stimulation, IMD 10 may deliver other types of therapy. For example, IMD 10 may deliver light pulses (e.g., optogenetic therapy) comprising a frequency selected based on one or more biomarkers of patient 12. In still further examples, IMD 10 may deliver ultrasound waves comprising a frequency selected based on one or more biomarkers of patient 12. In any case, the desynchronization pulse(s) may be configured to disrupt, or interfere with, at least a portion of the entrained electrical activity of patient 12.

Figure 2:
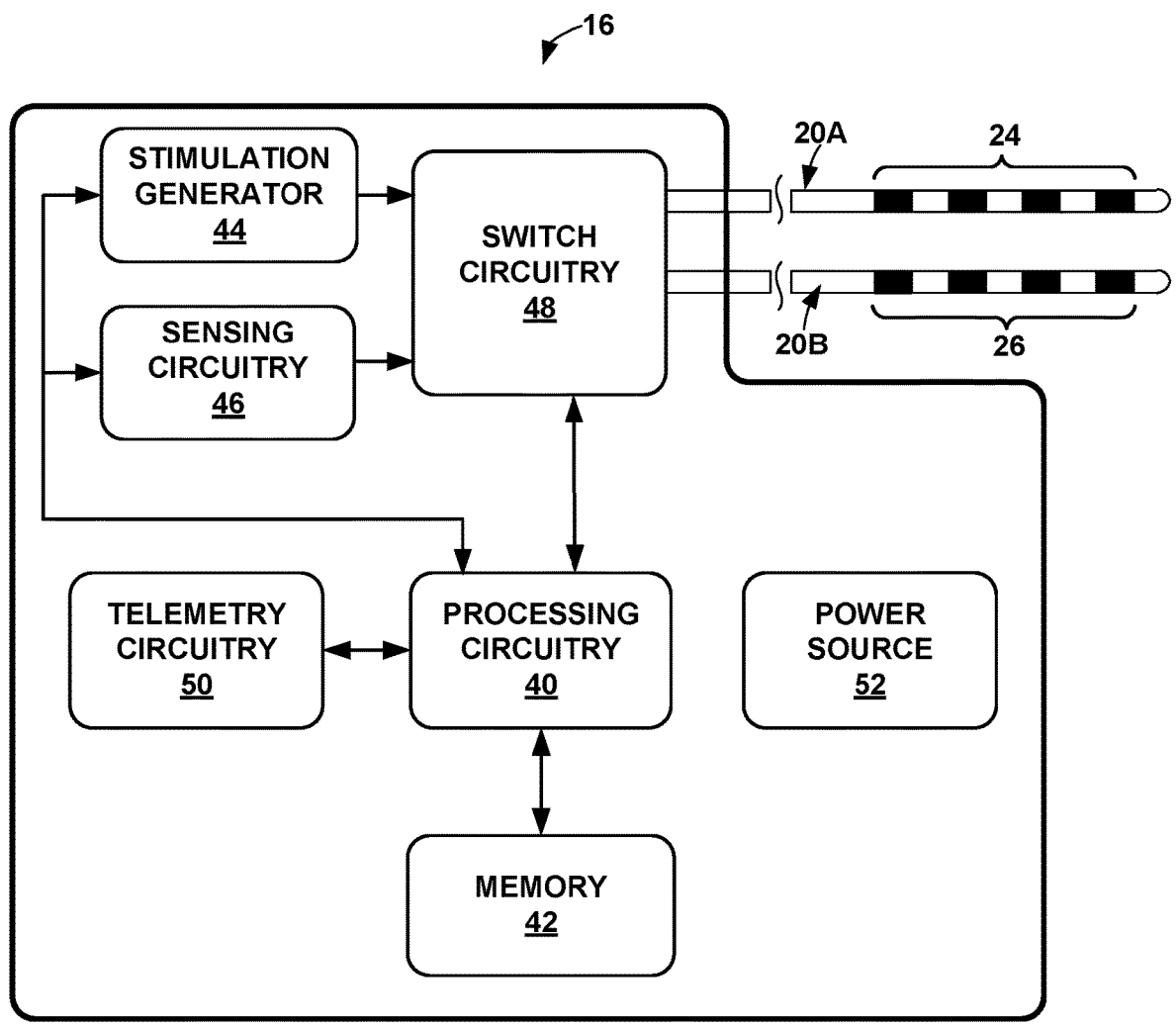
FIG. 2 is functional block diagram illustrating components of an example electrical stimulation system.

FIG. 2 is a functional block diagram illustrating components of an example IMD 16. In the example shown in FIG. 2, IMD 16 includes memory 42, processing circuitry 40, stimulation generator 44, sensing circuitry 46, switch circuitry 48, telemetry circuitry 50, and power source 52. Stimulation generator 44 and processing circuitry 40 may be contained within housing 17, along with the other circuitry and modules shown in the example of FIG. 2. Processing circuitry 40 may include any one or more microprocessors, controllers, digital signal processors (DSPs), application specific integrated circuits (ASICs), field-programmable gate arrays (FPGAs), discrete logic circuitry, or other processing circuitry. The functions attributed to processors described herein, including processing circuitry 40, may be provided by a hardware device and embodied as software, firmware, hardware, or any combination thereof.

In the example shown in FIG. 2, sensing circuitry 46 may be configured to sense bioelectrical brain signals of patient 12 via select combinations of electrodes 24, 26. Sensing circuitry 46 may include circuitry that measures the electrical activity of a particular region, e.g., an anterior nucleus, thalamus or cortex of brain 28 via select electrodes 24, 26. For treatment of Parkinson's disease, sensing circuitry 46 may be configured to measure the electrical activity of the subthalamic nucleus (STN), globus pallidus interna (GPi), globus pallidus externa (GPe), and/or other areas of the basal ganglia. For treatment of epilepsy, sensing circuitry 46 may be configured to measure the electrical activity of the one or more sites within the Circuit of Papez, including, e.g., anterior nucleus, internal capsule, cingulate, entorhinal cortex, hippocampus, fornix, mammillary bodies, or MMT.

Sensing circuitry 46 may sample the physiological signals substantially continuously or at regular intervals, such as, but not limited to, a frequency of about 1 Hertz to about 1000 Hertz, such as about 250 Hertz to about 1000 Hertz or about 500 Hertz to about 1000 Hertz. Sensing circuitry 46 includes circuitry for determining a voltage difference between two electrodes 24, 26, which generally indicates the electrical activity within the particular region of brain 28. One of the electrodes 24, 26 may act as a reference electrode, and, if sensing circuitry 46 is implanted within patient 12, housing 17 of IMD 16 or the sensing circuitry in examples in which sensing circuitry 46 is separate from IMD 16, may include one or more electrodes that may be used to sense physiological signals.

The output of sensing circuitry 46 may be received by processing circuitry 40. In some cases, processing circuitry 40 may apply additional processing to the physiological signals, e.g., convert the output to digital values for processing and/or amplify the physiological signals. In addition, in some examples, sensing circuitry 46 or processing circuitry 40 may filter the signal from the selected electrodes 24, 26 in order to remove undesirable artifacts from the signal, such as noise from cardiac signals generated within the body of patient 12. Although sensing circuitry 46 is incorporated into a common outer housing 17 with stimulation generator 44 and processing circuitry 40 in FIG. 2, in other examples, sensing circuitry 46 is in a separate housing and communicates with processing circuitry 40 via wired or wireless communication techniques. In some examples, physiological signals may be sensed via external electrodes (e.g., scalp electrodes).

In some examples, sensing circuitry 46 may include circuitry to tune to and extract a power level of a particular frequency band of a sensed physiological signal. Thus, the power level of a particular frequency band of a sensed physiological signal may be extracted prior to digitization of the signal by processing circuitry 40. By tuning to and extracting the power level of a particular frequency band before the signal is digitized, it may be possible to run frequency domain analysis algorithms at a relatively slower rate compared to systems that do not include a circuit to extract a power level of a particular frequency band of a sensed physiological signal prior to digitization of the signal. In some examples, sensing circuitry 46 may include more than one channel to monitor simultaneous activity in different frequency bands, i.e., to extract the power level of more than one frequency band of a sensed physiological signal. These frequency bands may include an alpha frequency band (e.g., 8 Hertz to 12 Hertz), beta frequency band (e.g., approximately 12 Hertz to approximately 35 Hertz), gamma frequency band (e.g., between approximately 35 Hertz to approximately 200 Hertz), or other frequency bands.

In some examples, sensing circuitry 46 may include an architecture that merges chopper-stabilization with heterodyne signal processing to support a low-noise amplifier. In some examples, sensing circuitry 46 may include a frequency selective signal monitor that includes a chopper-stabilized superheterodyne instrumentation amplifier and a signal analysis unit. Example amplifiers that may be included in the frequency selective signal monitor are described in further detail in commonly-assigned U.S. Patent Publication No. 2009/0082691 to Denison et al., entitled, "FREQUENCY SELECTIVE MONITORING OF PHYSIOLOGICAL SIGNALS" and filed on Sep. 25, 2008. U.S. Patent Publication No. 2009/0082691 to Denison et al., incorporated herein by reference in its entirety.

As described in U.S. Patent Publication No. 2009/0082691 to Denison et al., frequency selective signal monitor may utilize a heterodyning, chopper-stabilized amplifier architecture to convert a selected frequency band of a physiological signal to a baseband for analysis. The physiological signal may include a bioelectrical brain signal, which may be analyzed in one or more selected frequency bands to detect physiological signals oscillating at a pathological frequency and, in response, processing circuitry 40 may deliver electrical stimulation to entrain and disrupt the entrained electrical activity in accordance with some of the techniques described herein.

In some examples, sensing circuitry 46 may sense brain signals substantially at the same time that IMD 16 delivers therapy to patient 12. In other examples, sensing circuitry 46 may sense brain signals and IMD 16 may deliver electrical stimulation at different times.

In some examples, sensing circuitry 46 may monitor additional physiological signals. Suitable patient physiological signals may include, but are not limited to, muscle tone (e.g., as sensed via electromyography (EMG)), eye movement (e.g., as sensed via electrooculography (EOG) or EEG), and body temperature. In some examples, patient movement may be monitored via actigraphy. In one example, processing circuitry 40 may monitor an EMG signal reflective of the muscle tone of patient 12 to identify physical movement of the patient as a biomarker. In some examples, processing circuitry 40 may monitor the physical movement of a patient via one or more motion sensors that are included in IMD 16 and/or external to IMD 16 and transmit information to IMD 16 via telemetry circuitry 50.

In some examples, sensing circuitry 46 may monitor biomarkers that are indicative of symptoms of a disease, such as Parkinson's disease or epilepsy. For examples, sensing circuitry 46 may monitor one or more parameters indicative of muscle stiffness or movement (slow movement, tremor, and lack of movement) with may correspond to one or more symptoms of Parkinson's disease. Such parameters may be detected by EMG signals, actigraphy, accelerometers signals, and/or other suitable signal. In some examples, in response to the detection of one or more symptoms of Parkinson's disease based on the monitoring of such parameter(s), processing circuitry 40 may control stimulation generator 44 to generate electrical stimulation selected to entrain brain signals to oscillate at a particular frequency, and then adjust the frequency to disrupt portions of the entrained electrical activity that were or are oscillating at the particular entrainment.

Memory 42 may include any volatile or non-volatile media, such as a random access memory (RAM), read only memory (ROM), non-volatile RAM (NVRAM), electrically erasable programmable ROM (EEPROM), flash memory, and the like. Memory 42 may store computer-readable instructions that, when executed by processing circuitry 40, cause IMD 16 to perform various functions described herein. Memory 42 may be considered, in some examples, a non-transitory computer-readable storage medium comprising instructions that cause one or more processors, such as, e.g., processing circuitry 40, to implement one or more of the example techniques described in this disclosure. The term "non-transitory" may indicate that the storage medium is not embodied in a carrier wave or a propagated signal. However, the term "non-transitory" should not be interpreted to mean that memory 42 is non-movable. As one example, memory 42 may be removed from IMD 16, and moved to another device. In certain examples, a non-transitory storage medium may store data that can, over time, change (e.g., in RAM).

In the example shown in FIG. 2, the set of electrodes 24 of lead 20A includes four electrodes, and the set of electrodes 26 of lead 20B includes four electrodes. Processing circuitry 40 controls switch circuitry 48 to sense physiological signals with selected combinations of electrodes 24, 26. In particular, switch circuitry 48 may create or cut off electrical connections between sensing circuitry 46 and selected electrodes 24, 26 in order to selectively sense physiological signals, e.g., in particular portions of brain 28 of patient 12. Processing circuitry 40 may also control switch circuitry 48 to apply stimulation signals generated by stimulation generator 44 to selected combinations of electrodes 24, 26. For example, processing circuitry 40 may control stimulation generator 44 to generate stimulation pulses according to stimulation parameters. Processing circuitry 40 may then cause stimulation generator 44 to deliver the stimulation pulses to one or more electrodes 24, 26. In particular, switch circuitry 48 may couple stimulation signals to selected conductors within leads 20, which, in turn, deliver the stimulation signals across selected electrodes 24, 26. Switch circuitry 48 may be a switch array, switch matrix, multiplexer, or any other type of switching circuitry configured to selectively couple stimulation energy to selected electrodes 22A, 22B and to selectively sense bioelectrical brain signals with selected electrodes 24, 26. Hence, stimulation generator 44 is coupled to electrodes 24, 26 via switch circuitry 48 and conductors within leads 20. In some examples, however, IMD 16 does not include switch circuitry 48. In some examples, IMD 16 may include separate current sources and sinks for each individual electrode such that switch circuitry 48 may not be used.

Stimulation generator 44 may be a single channel or multi-channel stimulation generator. For example, stimulation generator 44 may be capable of delivering, a single stimulation pulse, multiple stimulation pulses, or a continuous signal at a given time via a single electrode combination or multiple stimulation pulses at a given time via multiple electrode combinations. In some examples, however, stimulation generator 44 and switch circuitry 48 may be configured to deliver multiple channels on a time-interleaved basis. For example, switch circuitry 48 may serve to time divide the output of stimulation generator 44 across different electrode combinations at different times to deliver multiple programs or channels of stimulation energy (e.g., entrainment stimulation pulses and desynchronization stimulation pulse(s)).

Telemetry circuitry 50 may support wireless communication between IMD 16 and programmer 14 or an external device 34 under the control of processing circuitry 40. In some instances, one of external device 34 may include an external data server (e.g., a remote server). For example, processing circuitry 40 of IMD 16 may transmit physiological signals, biomarkers, seizure probability metrics for particular sleep stages, a seizure probability profile for patient 12, etc. via telemetry circuitry 50 to telemetry circuitry within programmer 14 or external device 34. Accordingly, telemetry circuitry 50 may send information to programmer 14 on a continuous basis, at periodic intervals, or upon request from IMD 16 or programmer 14.

Power source 52 delivers operating power to various components of IMD 16. Power source 52 may include a rechargeable or non-rechargeable battery and in some cases, a power generation circuit. In some examples, power requirements may be small enough to allow IMD 16 to utilize patient motion and implement a kinetic energy-scavenging device to trickle charge a rechargeable battery.

In accordance with one or more examples of the disclosure, processing circuitry 40 and/or processing circuitry of another device (e.g., processing circuitry of programmer 14) may control sensing circuitry 46 to sense, via electrodes 24, 26, one or more oscillations of a physiological signal (e.g., a brain signal) associated with a pathological disease of patient 12. In some examples, the one or more oscillations are within a beta frequency range of about 11 Hertz to about 35 Hertz. In other examples, the one or more oscillations are within a Theta frequency band of about 4 Hertz to about 12 Hertz. In some examples, the one or more oscillations are associated with one or more symptoms of Parkinson's disease, such as tremor, rigidity, or bradykinesia, etc. In some examples, the one or more oscillations are associated with one or more symptoms of another disease, such as dystonia, essential tremor, Tourette's syndrome, obsessive compulsive disorder, epilepsy, or depression.

In some examples, processing circuitry 40 may determine a first set of stimulation parameters that define entrainment stimulation pulses configured to entrain electrical activity in brain 28 of patient 12. For example, processing circuitry 40 may receive stimulation parameters from another device via telemetry circuitry 50 and determine the stimulation parameters are to serve as the first plurality of stimulation parameters. In another example, processing circuitry 40 may perform various algorithms to determine the stimulation parameters to use to define the entrainment stimulation pulses. As such, processing circuitry 40 may cause stimulation generator 44 to deliver the entrainment stimulation pulses to at least one of electrodes 24, 26 according to the first plurality of stimulation parameters. In addition, processing circuitry 40 may determine a second set of stimulation parameters that define at least one desynchronization stimulation pulse configured to disrupt at least a portion of electrical activity entrained by the entrainment stimulation pulses. In such instances, processing circuitry may then cause stimulation generator 44 to deliver the at least one desynchronization stimulation pulse according to the second plurality of stimulation parameters. In some examples, processing circuitry 40 may cause the entrainment stimulation pulses to cease during delivery of the desynchronization pulses. In another example, processing circuitry 40 may cause the delivery of desynchronization pulses while the entrainment stimulation pulses are still being delivered (e.g., in parallel).

In some examples, in response to sensing the one or more oscillations of the physiological signals of patient 12, processing circuitry 40 and/or processing circuitry of another device (e.g., processing circuitry of external programmer 14) may determine the stimulation parameters for either the entrainment stimulation pulses, the desynchronization pulses, or both based on identified biomarkers. In one example, one or more external sensors may transmit physiological signals, via telemetry circuitry, to IMD 16, programmer 14, etc. For example, external sensors may be worn by patient 12 or may be external sensors that are otherwise configured to obtain physiological data from patient 12. For example, external sensors may sense movement information of patient 12 and transmit such information via telemetry circuitry. Processing circuitry 40 of IMD 16 may then utilize the physiological signal information in order to identify one or more biomarkers of patient 12. Processing circuitry 40 may use the identified biomarker information in order to determine patient-tailored stimulation parameters for the entrainment stimulation pulses, the desynchronization pulses, or both. In an example involving Parkinson's disease treatment, processing circuitry 40 may determine parameters of the desynchronization pulses so as to cause a decrease in the disease biomarker. As discussed herein, processing circuitry 40 may adjust these parameters over time depending on a status of the one or more disease biomarker over time (e.g., prevalent biomarker, decreasing biomarker, etc.) as may be indicated by physiological signal information. It will be understood that processing circuitry 40 may use such signals at the outset to determine initial stimulation parameters, as well as using such signals as feedback signals to further tailor the stimulation parameters over time.

Figure 3:
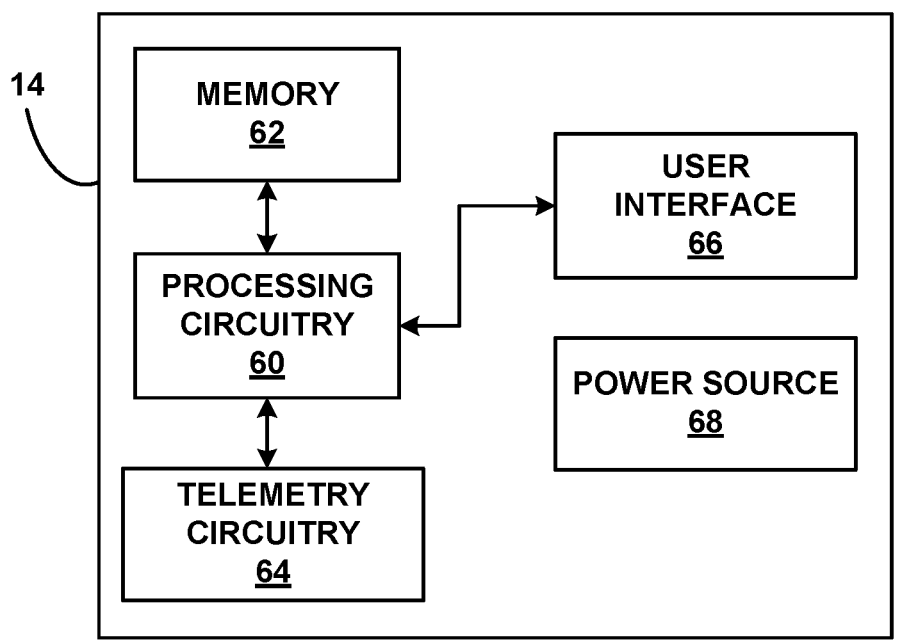
FIG. 3 is a functional block diagram illustrating components of an example medical device programmer.

FIG. 3 is a conceptual block diagram of an example external medical device programmer 14, which includes processing circuitry 60, memory 62, telemetry circuitry 64, user interface 66, and power source 68. Processing circuitry 60 controls user interface 66 and telemetry circuitry 64, and stores information and instructions to memory 62 and retrieves information and instructions from memory 62. Programmer 14 may be configured for use as a clinician programmer or a patient programmer. Processing circuitry 60 may comprise any combination of one or more processors including one or more microprocessors, DSPs, ASICs, FPGAs, or other equivalent integrated or discrete logic circuitry. Accordingly, processing circuitry 60 may include any suitable structure, whether in hardware, software, firmware, or any combination thereof, to perform the functions ascribed herein to processing circuitry 60.

A user, such as a clinician or patient 12, may interact with programmer 14 through user interface 66. User interface 66 includes a display (not shown), such as a LCD or LED display, touch screen, or other type of screen, to present information related to electrical stimulation, such as for a neuromodulation system or other type of electrical stimulation system. User interface 66 may also include an input mechanism to receive input, such as touch input, from the user. The input mechanisms may include, for example, buttons, a keypad (e.g., an alphanumeric keypad), a peripheral pointing device or another input mechanism that allows the user to navigate through user interfaces presented by processing circuitry 60 of programmer 14 and provide user input.

Memory 62 may include instructions for operating user interface 66 and telemetry circuitry 64, and for managing power source 68. Memory 62 may also store any therapy data received from IMD 16, such as biomarker information, physiological parameters (e.g., EMG signals, brain signals, etc.), etc. Memory 62 may further store stimulation parameters received from IMD 16 or delivered to IMD 16, such as during the course of therapy or electrical stimulation modulation. Memory 62 may include any volatile or nonvolatile memory, such as RAM, ROM, EEPROM or flash memory. In some examples, memory 62 may also include a removable memory portion.

Memory 62 may be considered, in some examples, a non-transitory computer-readable storage medium comprising instructions that cause one or more processors, such as, e.g., processing circuitry 60, to implement one or more of the example techniques described in this disclosure. The term "non-transitory" may indicate that the storage medium is not embodied in a carrier wave or a propagated signal. However, the term "non-transitory" should not be interpreted to mean that memory 62 is non-movable. As one example, memory 62 may be removed from programmer 14, and moved to another device. In certain examples, a non-transitory storage medium may store data that can change (e.g., in RAM).

Wireless telemetry in programmer 14 may be accomplished by RF communication or proximal inductive interaction of external programmer 14 with IMD 16. This wireless communication is possible through the use of telemetry circuitry 64. Telemetry circuitry 64 may be similar to the telemetry circuitry of IMD 16. In some examples, programmer 14 may be configured to communicate through a wired connection. In this manner, other external devices, such as IMD 16, may be configured to communicate with programmer 14 through a wired and/or wireless connection.

Power source 68 may deliver operating power to the components of programmer 14. Power source 68 may include a battery and in some instances, a power generation circuit. In some examples, power source 68 may be rechargeable.

In some examples, a user, such as one or more of a clinician or patient 12, may access and configure IMD 16 via user interface 66 of programmer 14. For example, a clinician may program, via user interface 66 of programmer 14, one or more electrical stimulation parameters that define entrainment stimulation pulses and/or that define desynchronization stimulation pulse(s). Programmer 14 may deliver, via telemetry circuitry 64, the programmed electrical stimulation parameters to IMD 16. Further, the clinician may adjust the one or more electrical stimulation parameters of electrical stimulation delivered by IMD 16. In some examples, programmer 14 or IMD 16 may automatically adjust the electrical stimulation parameters. In one example, processing circuitry 60 of programmer 14 may alter, based on feedback received from IMD 16, the amount of time defined for one or more desynchronization stimulation pulse(s), the number of desynchronization stimulation pulse(s) scheduled for delivery electrodes 24, 26, a frequency and/or amplitude of the desynchronization stimulation pulse(s), a duty cycle of the desynchronization stimulation pulse(s), or one or more other stimulation parameters. Processing circuitry 60 may then deliver the one or more altered stimulation parameters to IMD 16 for execution. In some examples, processing circuitry 60 may receive user input that the electrical stimulation therapy is to operate in either an open loop configuration, a closed loop configuration, or an open loop configuration that progresses to a closed loop configuration. For example, a user may select via user interface 66 an option to implement any one of these configurations for delivery of electrical stimulation to patient 12.

Figure 4:
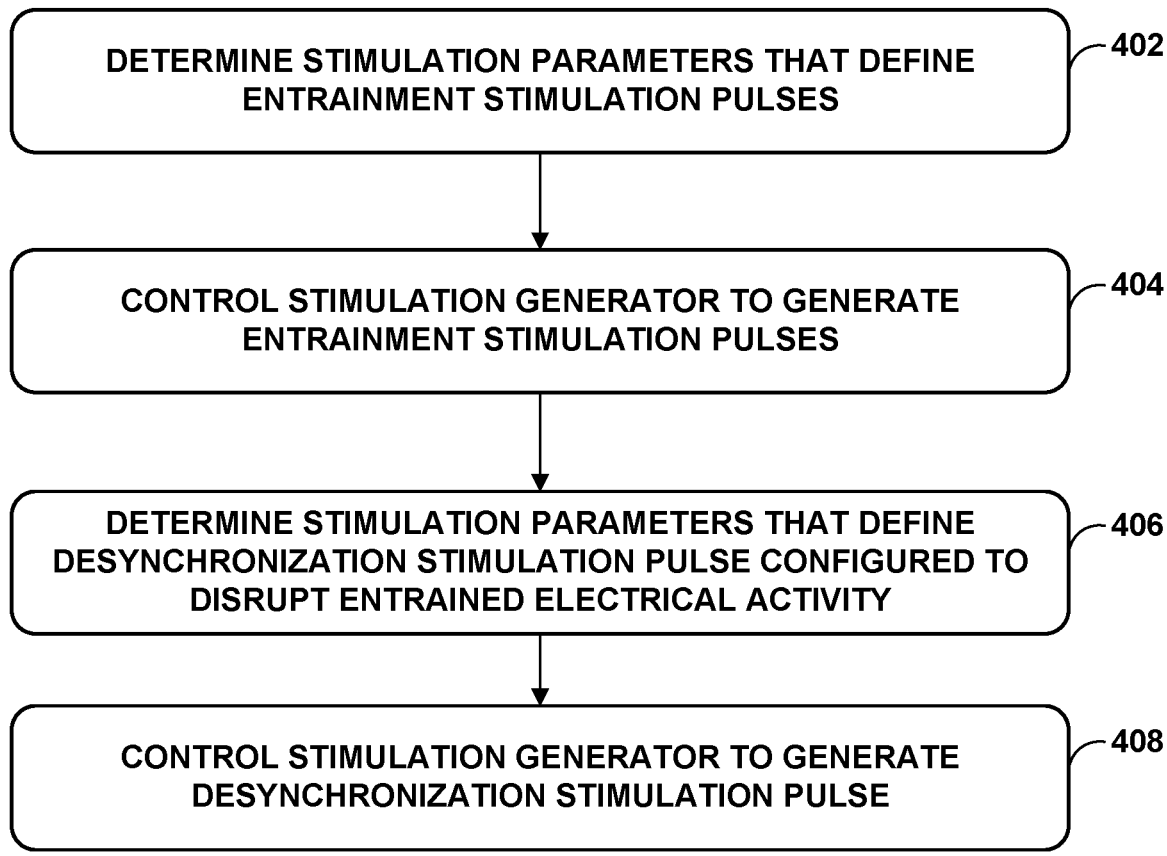
FIG. 4 is a flow diagram illustrating an example operation for delivering electrical stimulation to the brain of a patient in accordance with one or more techniques of the disclosure.

FIG. 4 is a flow diagram illustrating an example operation for delivering electrical stimulation to the brain of a patient. For ease of illustration the example of FIG. 4 is described with reference to therapy system 10 of FIG. 1. However, the techniques of this disclosure are not so limited, and may be employed in other suitable systems or devices configured to deliver electrical stimulation to one or more regions of patient 12, including spinal cord regions, muscle tissue regions, etc. In addition, while described with reference to processing circuitry 40 of IMD 16 as performing the techniques of FIG. 4, the techniques of this disclosure are not so limited, and in some instances, the techniques of this disclosure may be performed by processing circuitry of another suitable device, such as processing circuitry 60 of programmer 14 or processing circuitry of a remote server. For example, processing circuitry 60 may transmit electrical stimulation parameters (e.g., amplitudes, durations, electrode polarity, etc.) to IMD 16 via telemetry circuitry 64. Likewise, processing circuitry 60 may transmit information to programmer 14 via telemetry circuitry 50, such as by communicating information relating to biomarkers, feedback signals, stimulation parameters, pathology information, physiological signals, etc. In any event, a person skilled in the art will understand that various examples are used for illustration purposes and that other implementation examples may be achieved within the scope of this disclosure.

In one example, processing circuitry, such as that of IMD 16 or programmer 14, may determine a first set of stimulation parameters that define entrainment stimulation pulses (402). For example, processing circuitry 40 may determine a first set of stimulation parameters that define entrainment stimulation pulses (e.g., an entrainment stimulation pulse train). The entrainment stimulation may be configured to entrain electrical activity in patient 12 (e.g., in the brain of patient 12). The stimulation parameters may include a frequency parameter, a pulse width parameter, a voltage amplitude parameter, current amplitude parameter, a duration parameter, etc. For example, processing circuitry 40 may determine a length of time for delivering a first entrainment stimulation pulse train to one or more electrode(s), such as to at least one of electrode(s) 24, 26.

In some examples, the first set of stimulation parameters that define the entrainment stimulation pulses include frequency ranges that are less than or equal to 100 Hertz. For example, the entrainment stimulation pulses may be delivered at a frequency of 5 Hertz to 80 Hertz. The stimulation pulses may be biphasic. In addition, stimulation parameters that define the entrainment stimulation pulses may include pulse width ranges. For example, the pulse width ranges for the entrainment stimulation pulses may include a pulse width of 30 microseconds to 300 microseconds. In addition, stimulation parameters that define the entrainment stimulation pulses may include amplitude ranges. For example, the amplitude ranges for the entrainment stimulation pulses may include an amplitude of 0.1 to 10 Volts or 0.1 to 25 milliamps. For example, the amplitude ranges for the entrainment stimulation pulses may include an amplitude of 3.5 Volts. In one example, the entrainment stimulation pulses may include a frequency selected from a range of about 2 Hertz to about 150 Hertz, and a pulse width selected from about 30 microseconds to about 300 microseconds. In one example of a current-controlled system, the entrainment stimulation pulses may include a current amplitude selected from about 0.2 milliamps to about 10 milliamps and a pulse width selected from about 30 microseconds to about 300 microseconds. In another example, the entrainment stimulation pulses may include a current amplitude selected from about 0.1 milliamps to about 25 milliamps and a pulse width selected from about 30 microseconds to about 300 microseconds. In such examples, processing circuitry 40 may deliver the entrainment stimulation pulses at a frequency selected from a range of about 2 Hertz (e.g., ±1 Hertz) to about 150 Hertz (e.g., ±10 Hertz).

In some examples, processing circuitry 40 may control stimulation generator 44 to generate the entrainment stimulation pulses (404). For example, processing circuitry 40 may control stimulation generator 44 to generate the entrainment stimulation pulses according to the first set of stimulation parameters determined to define the entrainment stimulation pulses. In some examples, processing circuitry 40 may cause stimulation generator 44 to deliver the entrainment stimulation pulses to at least one electrode, such as one of electrode(s) 24, 26 or combination of electrode(s) 24, 26. In some examples, the stimulation parameters that define the entrainment stimulation pulses may be configured to both entrain electrical activity and cause destructive interference within one or more regions of brain 28 of patient 12. That is, the entrainment stimulation pulses may also provide some degree of therapy to patient 12.

In some examples, processing circuitry 40 may determine a second set of stimulation parameters for one or more desynchronization stimulation pulse(s) (e.g., a desynchronization stimulation pulse train) (406). In some instances, the stimulation parameters that define the desynchronization stimulation pulse(s) may be patient tailored. In any case, the desynchronization stimulation pulse(s) may be configured to disrupt at least a portion of electrical activity of the brain entrained by the entrainment stimulation pulses. In some examples, the desynchronization stimulation pulse(s) may cause neurons or cells to transmit electrical signals at irregular intervals relative to regularity inherent in entrained electrical activity or otherwise, out of synchrony with the entrained electrical activity.

In some examples, the second set of stimulation parameters defining the desynchronization stimulation pulse(s) may be different from the first set of stimulation parameters defining the entrainment stimulation pulses. For example, the first set of stimulation parameters that define the entrainment stimulation pulses may include a first pulse frequency below approximately 100 Hertz (e.g., 100 Hertz±5 Hz). The second set of stimulation parameters that define the desynchronization stimulation pulse(s) may include a second pulse frequency of above or equal to approximately 100 Hertz. For example, the desynchronization stimulation pulses may be generated at a second pulse frequency between approximately 30 Hertz and 125 Hertz higher than the first pulse frequency. In some examples, the desynchronization stimulation pulse(s) may include a frequency selected from a range of about 2 Hertz (e.g., ±1.9 Hertz) to about 200 Hertz (e.g., ±5 Hertz) or from a range of about 100 Hertz (e.g., ±5 Hertz) to about 200 Hertz (e.g., ±5 Hertz). The stimulation pulses may be biphasic. In addition, stimulation parameters that define the desynchronization stimulation pulse(s) may include pulse width ranges. In one non-limiting example, the pulse width that defines a set of desynchronization stimulation pulse(s) may include a pulse width selected from a range of between 20 microseconds (µs) and 450 µs. For example, the pulse width that defines a set of desynchronization stimulation pulse(s) may include a pulse width selected from a range of between 20 µs and 60 µs, between 20 µs and 90 µs, between 20 µs and 120 µs, between 60 µs and 90 µs, between 60 µs and 120 µs, between 60 µs and 450 µs, between 90 µs and 120 µs, between 90 µs and 450 µs, or between 120 µs and 450 µs. In some examples, the pulse width ranges may be selected from ranges that include pulse widths that are less than 20 µs or are greater than 450 µs. In one example, a pulse width that defines a set of desynchronization stimulation pulse(s) may be 75 µs or 85 µs, and may have been selected from one or more of the example ranges above, such as from the range of between 20 µs and 450 µs, between 70 µs and 90 µs, or between 60 µs and 120 µs, etc.

In addition, stimulation parameters that define the desynchronization stimulation pulse(s) may include amplitude ranges. For example, the amplitude ranges for the desynchronization stimulation pulse(s) may include an amplitude of 0.1 to 10 Volts or 0.1 to 25 milliAmps. In one example, the desynchronization stimulation pulse(s) may include a frequency selected from a range of about 2 Hertz to about 200 Hertz, and a pulse width selected from about 30 microseconds to about 300 microseconds. In one example of a current-controlled system, the desynchronization stimulation pulse(s) may include a current amplitude selected from a range of about 0.2 milliamps (e.g., ±0.1 milliamps) to about 10 milliamps (e.g., ±3 milliamps).

Subsequent to generating the entrainment stimulation pulses, processing circuitry 40 may control stimulation generator 44 to generate the at least one desynchronization stimulation pulse according to the second set of stimulation parameters (408). In one example, processing circuitry 40 may cause stimulation generator 44 to deliver the desynchronization stimulation pulse(s) to the same electrode or combination of electrodes used for the entrainment stimulation pulses. In some examples, processing circuitry 40 may cause stimulation generator 44 to deliver the at least one desynchronization stimulation pulse to a different one of electrode(s) 24, 26 or combination of electrode(s) 24, 26 relative to the electrode(s) used for the entrainment stimulation pulses.

In some examples, processing circuitry 40 may transition between the entrainment stimulation pulses and the desynchronization stimulation pulse(s) by varying a duty cycle, pulse width, frequency, and/or amplitude of stimulation generator 44. For example, processing circuitry 40 may transition between the entrainment pulses and the desynchronization stimulation pulse(s) by varying a duty cycle (e.g., ratio of 'on' time to 'off' time) of stimulation generator 44. In such examples, processing circuitry 40 may vary the duty cycle for a digital signal (e.g., the described pulses), rather than an analog waveform. In another example, processing circuitry 40 may vary an analog waveform when transitioning between the entrainment pulses and the at least one desynchronization stimulation pulse. In either case, the second set of stimulation parameters defining the desynchronization stimulation pulse(s) may include at least one parameter that is varied from at least one corresponding parameter included with the first set of stimulation parameters defining the entrainment stimulation pulses. For example, the varied parameter may include one or more of a varied amplitude, pulse width, frequency, and/or in some cases, a varied duty cycle. In an illustrative example, the second set of stimulation parameters may include a second frequency that is varied or different from a first frequency included with a different set of stimulation parameters defining a different phase or set of stimulation pulses.

In examples where the entrainment stimulation pulses continue during the desynchronization phase, processing circuitry 40 may control stimulation generator 44 to generate the desynchronization stimulation pulse(s) while simultaneously controlling stimulation generator 44 to generate the desynchronization stimulation pulse(s), without causing stimulation generator 44 to transition between the entrainment stimulation pulses and the desynchronization stimulation pulse(s).

In an illustrative example, processing circuitry 40 may cause the stimulation generator to deliver the entrainment stimulation pulses to a first one of electrodes 24, 26, then cause the stimulation generator to deliver the at least one desynchronization stimulation pulse to a second one of electrodes 24, 26. In this way, stimulation generator 44 via processing circuitry 40 may target a smaller volume within a larger volume entrained by the entrainment stimulation pulses. In some examples, the first set of stimulation parameters that define the entrainment stimulation pulses may be configured to entrain electrical activity of a first region of brain 28. As such, the second set of stimulation parameters that define the desynchronization pulse(s) may be configured to cause destructive interference for at least a portion of the entrained electrical activity within a second region of brain 28. The second region of brain 28 may be smaller than the first region of brain 28. In addition, the second region of brain 28 may be found within at least a portion of the first region of brain 28.

In another example, processing circuitry 40 may deliver electrical stimulation based on feedback received regarding the entrained activity. For example, processing circuitry 40 may cause stimulation generator 44 to deliver the entrainment stimulation pulses to a first one of electrodes 24, 26. Processing circuitry 40 may then receive indication that the entrainment stimulation pulses have resulted in electrical activity being entrained in patient 12. Responsive to determining that the entrainment stimulation pulses have resulted in electrical activity being entrained in patient 12, processing circuitry 40 may cause stimulation generator 44 to deliver the at least one desynchronization stimulation pulse to a second one of electrodes 24, 26.

In addition, processing circuitry 40 may continue to alternate between the entrainment stimulation pulse phase and desynchronization pulse phase. In some examples, processing circuitry 40 may adjust, automatically or otherwise, parameters of either pulse phase as time progresses.

While described with reference to processing circuitry 40 of IMD 16, the techniques of this disclosure are not so limited, and the techniques of this disclosure may be implemented by other processing circuitry (alone or in combination with processing circuitry of another device), such as processing circuitry 60 of programmer 14 or processing circuitry of external device 34 or an external server. For example, processing circuitry 60 may determine stimulation parameters and transmit the stimulation parameters to IMD 16, thereby causing IMD 16 (e.g., stimulation generator 44) to deliver the electrical stimulation pulses. In addition, it will be understood that some techniques of FIG. 4 may be combined or omitted altogether. For example, processing circuitry, such as that of IMD 16, may determine stimulation parameters to define the entrainment stimulation pulses and the desynchronization stimulation pulse(s) in parallel, before or during the delivery of electrical stimulation to patient 12.

Figure 5:
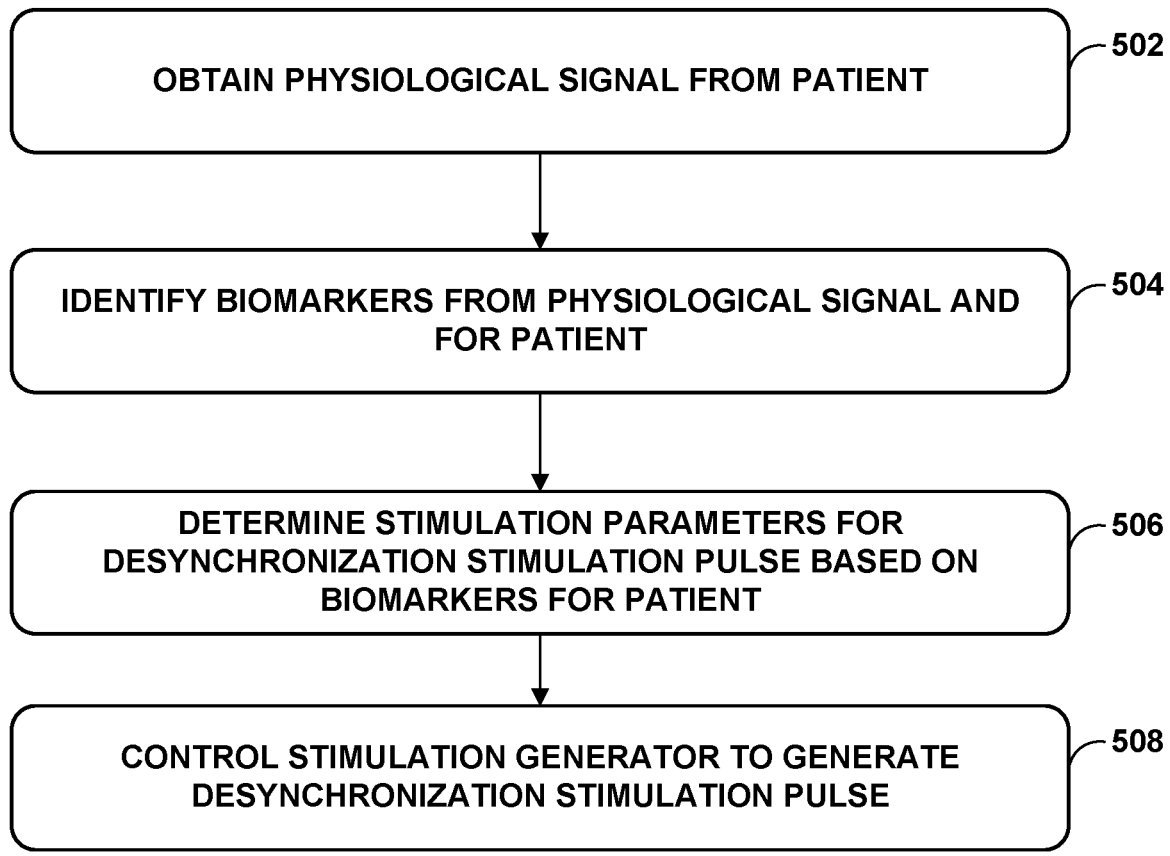
FIG. 5 is a flow diagram illustrating an example operation for delivering electrical stimulation to the brain of a patient by utilizing biomarkers of the patient in accordance with one or more techniques of the disclosure.

FIG. 5 is a flow diagram illustrating an example operation for delivering electrical stimulation to the brain of a patient by utilizing biomarkers of the patient. Biomarkers may be used to determine stimulation parameters for either entrainment stimulation pulses, desynchronization stimulation pulse(s), other phases of the electrical stimulation (e.g., a rest phase duration).

In an example where biomarkers are used to determine stimulation parameters that define desynchronization stimulation pulse(s), processing circuitry 40 may control stimulation generator 44 to generate entrainment stimulation pulses (with or without biomarker tailoring). In such examples, processing circuitry 40 may obtain a physiological signal from a patient (502). For example, the physiological signal may be a brain wave signal. In some examples, the physiological signal may be a tremor signal, such as a signal corresponding to movement of a limb. In some examples, the physiological signal may be a local field potential (LFP) signal originating from within one or more regions of the brain.

Processing circuitry 40 may identify one or more biomarkers from the physiological signal and for patient 12 (504). In some examples, processing circuitry 40 may be configured receive the physiological signal or, in some cases, the one or more biomarkers, from an external device 34 or from an external server that stores biomarkers for patient 12 received from other devices, such as an external device 34. In some examples, external device 34 may be external to and distinct from housing 17. For example, external device 34 may be a wearable device. In other examples, the external device may be external to therapy system 10 of FIG. 1. In some examples, external device 34 may be a sensing device configured to detect physiological signals from patient 12. In any case, external device 34 may be configured to obtain a physiological signal from patient 12. External device 34 may then communicate, via telemetry circuitry of external device 34, attributes of the physiological signal to IMD 16 or programmer 14. In another example, external device 34 may identify one or more biomarkers from the physiological signal and communicate, via telemetry circuitry of external device 34, to IMD 16 or programmer 14. In some instances, programmer 14 may communicate, via telemetry circuitry 64, the physiological signal attributes, or the one or more biomarkers, to IMD 16 for further processing. In any case, processing circuitry 40 may be configured to obtain the physiological signal from patient 12, either directly or indirectly, such as from external device 34 or programmer 14.

In one example, the physiological signal may be a local field potential (LFP) signal. In such examples, processing circuitry 40 may identify the one or more biomarkers from the LFP of patient 12. As such, the one or more biomarkers may indicate a neural state of patient 12 (e.g., tremors). An example tremor may include physical manifestations of brain activity, such that the LFP biomarkers may indicate that a tremor in brain 28 of patient 12 is occurring when a power level within a particular frequency band, such as a beta frequency band, is high. In some examples, the biomarkers may be indicative of a neural state of patient 12 comprising a frequency between approximately 0.1 Hertz to 500 Hertz. In such examples, such frequencies may span the above range or in some cases, beyond the range, as high frequency oscillations (HFOs) may also indicate the neural state of patient 12. It has been observed that particular LFP signals lie in the range of 0.1 Hertz to 500 Hertz. For example, low frequency (e.g., 5-10 Hertz) may indicate tremor frequencies or conditions, beta frequencies indicating Parkinson's disease rigidity, gamma frequencies correlating to dyskinesia, and so forth.

In an illustrative example, processing circuitry 40 may receive one or more tremor signals from within one or more regions of brain 28 of patient 12. The one or more tremor signals may be configured to indicate tremors in a local field potential (LFP) of patient 12. As mentioned above, the one or more tremor signals include frequencies between 0.1 Hertz and 500 Hertz. As such, processing circuitry 40 may identify a biomarker between 0.1 Hertz and 500 Hertz relating to tremors in the LFP of patient 12. Processing circuitry may use such a biomarker in order to determine the stimulation parameters for the one or more electrical stimulation pulses. In some examples, processing circuitry 40 may utilize a LFP biomarker to determine the direction and relative distance in which the greatest local synchrony occurs. Processing circuitry 40 then tailor the desynchronization pulse and the directionality of the desynchronization pulse to include the highly synchronized region. While described with reference to LFP tremors, the techniques of this disclosure are not so limited, and various other biomarkers may be determined, such as beta biomarkers, EEG signal biomarkers, ECoG signal biomarkers, wearable input signal biomarkers, physical tremor biomarkers, brain electrical signal biomarkers, etc.

For example, processing circuitry 40 may determine stimulation parameters that define the desynchronization stimulation pulse(s) based at least in part on the one or more biomarkers for patient 12 (506). In such examples, processing circuitry 40 may control stimulation generator 44 to generate desynchronization stimulation pulse(s) (508). For example, processing circuitry 40 may cause stimulation generator 44 to deliver desynchronization stimulation pulse(s) to one of electrode(s) 24, 26 according to the stimulation parameters determined based on the one or more biomarkers. In any case, processing circuitry 40 may use biomarker information to determine stimulation parameters for entrainment stimulation parameters and/or desynchronization stimulation parameters. For example, processing circuitry 40 may use biomarker information to determine only the desynchronization stimulation parameters, whereas the entrainment stimulation parameters may be predefined, such as by a physician or clinician, and/or retrieved from memory, such as from a database of preset or predefined stimulation parameters.

While described with reference to processing circuitry 40 of IMD 16, the techniques of this disclosure are not so limited, and the techniques of this disclosure may be implemented by other processing circuitry (alone or in combination with processing circuitry of another device), such as processing circuitry 60 of programmer 14 or processing circuitry of external device 34 or an external server. For example, processing circuitry 60 may receive and/or identify one or more biomarkers, determine one or more stimulation parameters based on the one or more biomarkers, and transmit stimulation parameters to IMD 16, thereby causing IMD 16 (e.g., stimulation generator 44) to deliver the electrical stimulation pulses. In addition, it will be understood that some techniques of FIG. 5 may be combined or omitted altogether. For example, processing circuitry, such as that of IMD 16, may determine stimulation parameters to define the entrainment stimulation pulses and the desynchronization stimulation pulse(s) in parallel, before or during the delivery of electrical stimulation to patient 12, based on one or more biomarkers of patient 12. That is, processing circuitry 40 may identify one or more biomarkers before or during the delivery of electrical stimulation pulses to patient 12.

Figure 6:
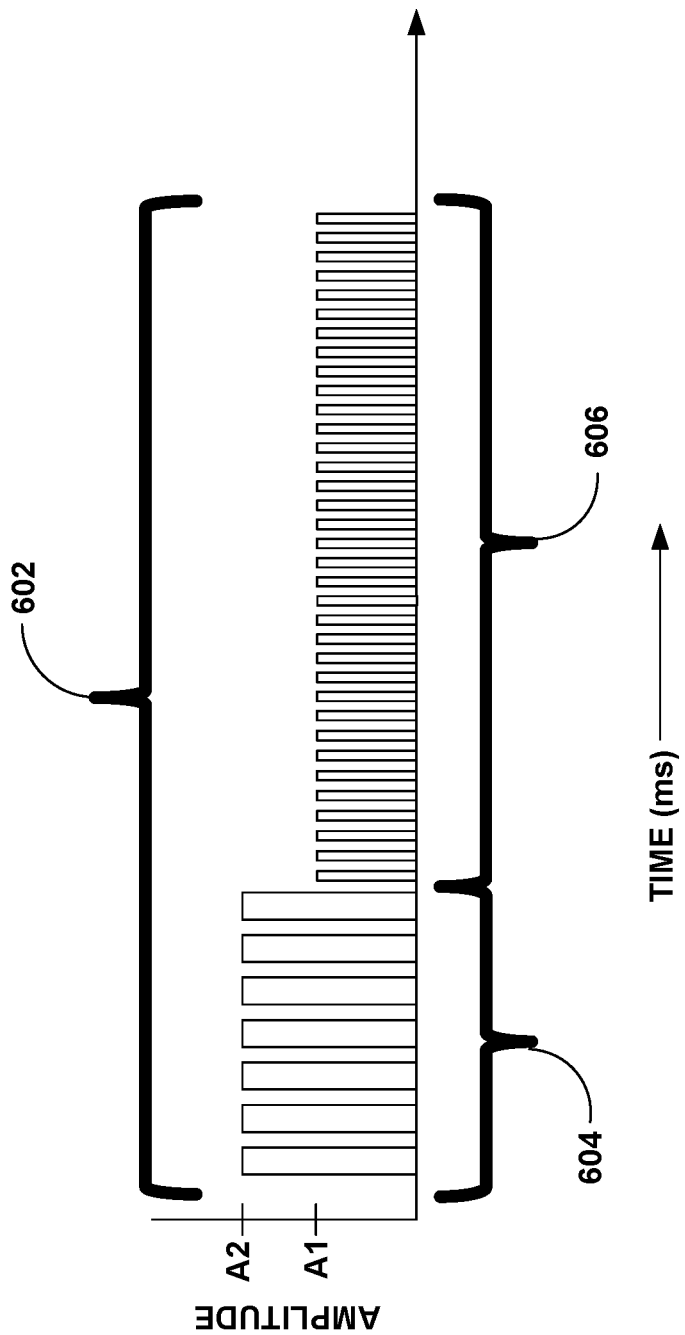
FIG. 6 is a chart illustrating example modulation of electrical stimulation pulses in accordance with one or more techniques of the disclosure.

FIG. 6 is a chart illustrating example modulation of electrical stimulation pulses 602. FIG. 6 illustrates entrainment stimulation pulses 604 and desynchronization stimulation pulses 606. Processing circuitry 40 may cause stimulation generator 44 to deliver the entrainment stimulation pulses 604 according to a first plurality of stimulation parameters including a first stimulation frequency. In addition, processing circuitry 40 may cause stimulation generator 44 to deliver the desynchronization stimulation pulses 604 according to a second plurality of stimulation parameters including a second stimulation frequency. In some examples, the first stimulation frequency is different from the second stimulation frequency. For example, the first stimulation frequency may be lower than the second stimulation frequency for the desynchronization stimulation pulses 606. In some examples, the stimulation parameters may include a duration parameter or in some instances, a pulse count parameter. In such examples, processing circuitry 40 may determine one or more scaling factors. Processing circuitry 40 may apply the scaling factors to the patient-specific biomarkers to determine the stimulation parameters to define each stimulation phase. For example, processing circuitry 40 may determine scaling factors a, b, and c. These scaling factors may be all different scaling factors, whereas in some instances, some scaling factors may be the same. In such instances, processing circuitry 40 may determine stimulation parameters to define each stimulation phase using the following equations: $f\_1 = a * f\_patient$ (e.g., a duration component of pulses of multiple phases 602), $f\_2 = b * f\_patient$ (e.g., a duration component of pulses 604), and $f\_3 = c * f\_patient$ (e.g., a duration component of pulses 606). In such examples, f_patient is the patient specific physiological signal, such as a signal received or retrieved from one of external devices 34 or programmer 14.

In some examples, processing circuitry 40 may determine that a duration parameter has been satisfied by counting the number of pulses, in conjunction with a reference to the frequency of the pulses (e.g., how many pulses per second or per millisecond). In any case, the duration parameter or pulse count parameter for the entrainment stimulation pulses 604, the desynchronization stimulation pulses 604, or both entrainment stimulation pulses 604 the desynchronization stimulation pulses 604 may be tailored to each particular patient 12 (e.g., based on physiological signals obtained from patient 12, based on patient history of patient 12, etc.). Processing circuitry 40, for each case, may selected the duration parameter or pulse count parameter from a range having an upper limit and a lower limit. In a non-limiting example, processing circuitry 40 may cause the entrainment stimulation pulses 604 to be delivered between 1 ms and 40 ms or until processing circuitry 40 determines an entrainment indication, such as from a signal received from an external wearable device or other internal device. In such instances, processing circuitry 40 may tailor the duration or pulse count parameter to patient 12 such that the tailored parameters fall within an acceptable range for treatment of patient 12.

In such examples, processing circuitry 40 may be configured to increase the first stimulation frequency to reach the second stimulation frequency. For example, the first stimulation frequency may be at or below 100 Hertz. In such examples, processing circuitry 40 may increase the first stimulation frequency by a first amount in order to achieve a second stimulation frequency for the desynchronization stimulation pulses 606. In a non-limiting example, the first amount may be between around 30 Hertz and 125 Hertz. In the example of FIG. 6, the amplitude and pulse width of entrainment stimulation pulses 604 are greater than the amplitude and pulse width of desynchronization stimulation pulses 606. However, the amplitudes and/or pulse widths may be the same or higher for desynchronization stimulation pulses 606 in other examples. It will be understood that the example rising and fallings edge of a square-like pulse as in FIGS. 6, 7, 11, 12, and 13 are shown for illustration purposes, and that aspects of this disclosure are not so limited. For example, the pulses may be configured as saw, triangle, or other non-sinusoidal pulses or non-sinusoidal waveforms. That is, processing circuitry 40 may cause stimulation generator 44 to deliver stimulation in the form of saw pulses, triangle pulses, square pulses (e.g., rectangular pulses), etc.

Figure 7:
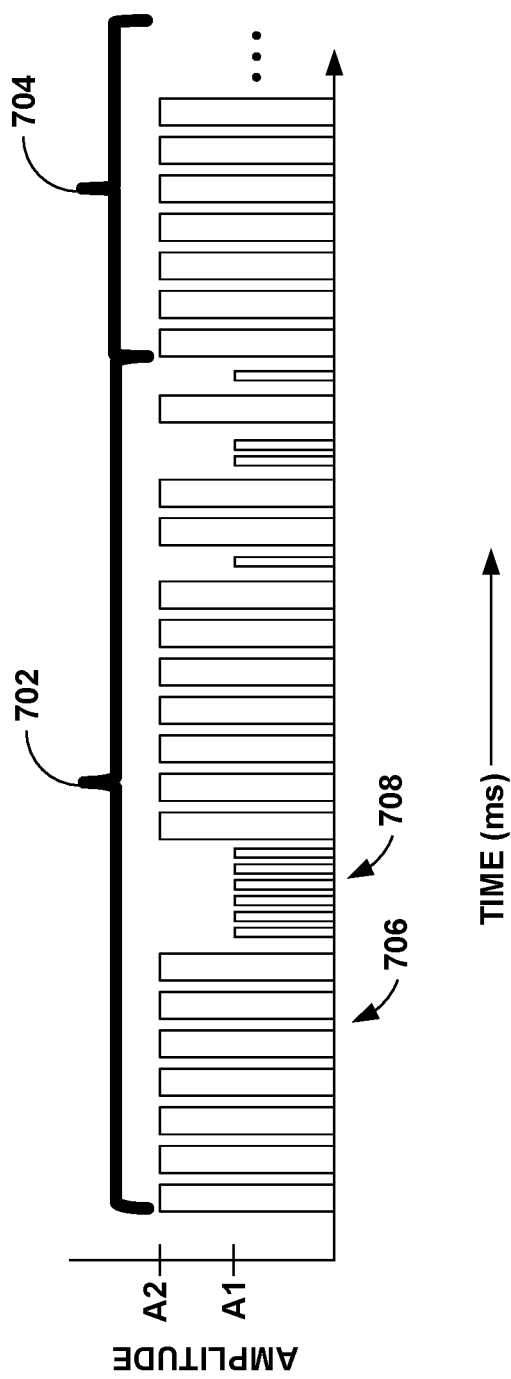
FIG. 7 is a chart illustrating example modulation of electrical stimulation pulses in accordance with one or more techniques of the disclosure.

FIG. 7 is a chart illustrating example modulation of electrical stimulation pulses that repeat over time. For example, processing circuitry 40 may cause stimulation generator 44 to deliver a first set of stimulation pulses 702 and repeat the stimulation pulses as a repeating set of stimulation pulses 704. The first set and the repeating set of stimulation pulses may include entrainment stimulation pulses 706 and desynchronization stimulation pulses 708, similar to entrainment stimulation pulses 604 and desynchronization stimulation pulses 606 from FIG. 6. As shown, the duration and/or pulse count of different phases or between phases may not be uniform throughout a repeating set of stimulation pulses 704.

Figure 8:
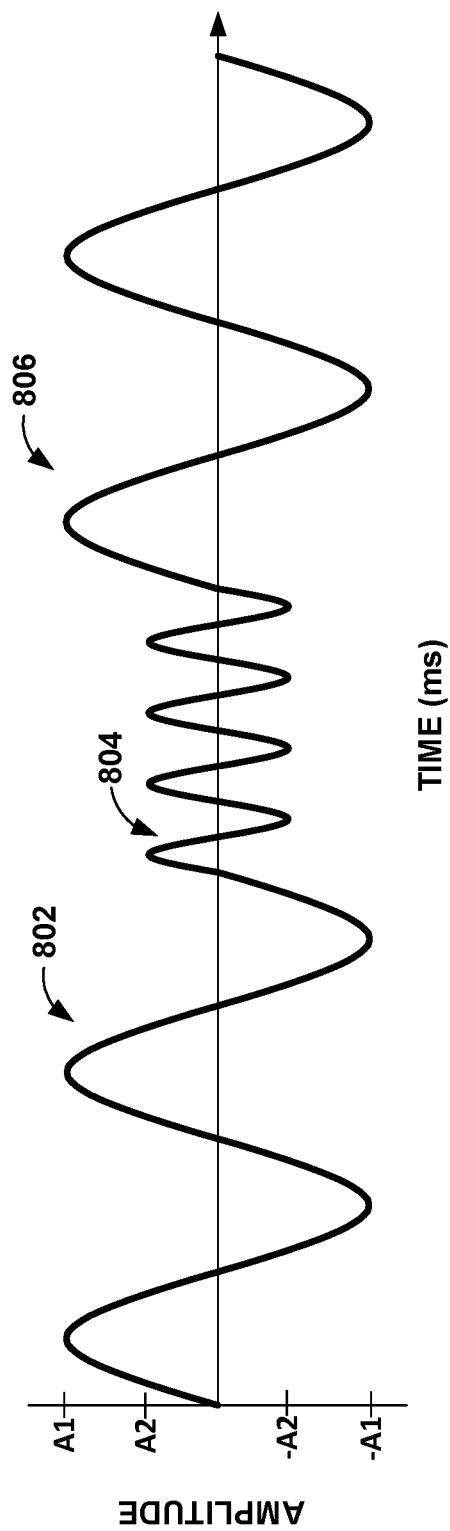
FIG. 8 is a chart illustrating an example electrical stimulation waveform being modulated in accordance with one or more techniques of the disclosure.

FIG. 8 is a chart illustrating an example electrical stimulation waveform modulated to include different frequencies over time. The example of FIG. 8 illustrates entrainment stimulation waveform 802 and desynchronization stimulation waveform 804 being delivered in an open loop configuration (e.g., not changing over time based on efficacy of stimulation therapy). That is, processing circuitry 40 may be configured to perform electrical stimulation modulation in an open loop configuration by interleaving entrainment stimulation waveform 802 and desynchronization stimulation waveform 804. Waveforms 802, 804 may be defined by different amplitude, frequency, or other stimulation parameters. In the examples shown in FIGS. 8, 9, 14 and 15, the example waveforms are shown as stimulation signals for illustration purposes. It will be understood that the stimulation signals may be generated and delivered as pulses instead, for example, as shown in FIG. 6. That is, the examples shown in FIGS. 8, 9, 14 and 15 are intended to illustrate a change in frequency, amplitude, etc., but the actual stimulation may not necessarily be delivered as a sinusoid signal. For example, the example waveform of stimulation signals in FIG. 9 may translate to a stimulation pulse train similar to that shown, for example, in certain portion of FIG. 7. That is, the example waveforms may be delivered as pulses, although shown as waves, in some instances, for illustration purposes.

As shown, entrainment stimulation waveform 802 may have a first amplitude and frequency, whereas desynchronization stimulation waveform 804 may have different stimulation parameters (e.g., higher frequency, lower amplitude, etc.). In some examples, including in the example waveform shown in FIG. 8, entrainment stimulation waveform 802 and desynchronization stimulation waveform 804 may have the same frequency with different amplitudes. That is, entrainment stimulation waveform 802 may have an amplitude of A1 and desynchronization stimulation waveform 804 may have an amplitude of A3 (not shown). In such examples, entrainment stimulation waveform 802 and the desynchronization stimulation waveform 804 may share a same or substantially the same frequency, such as within 5 to 10 Hz of one another. In some examples, A3 may be greater than A1. A3 may, in some instances however, be less than A1.

The amplitude of FIG. 8 may be in units of volts or amps depending on the configuration of the electrical stimulation therapy, such as based on whether the electrical stimulation is based on electrical current (e.g., mA) or voltage (e.g., V). The time axis of FIG. 8 may be in units of milliseconds. In some examples, processing circuitry 40 may be configured to control stimulation generator 44 to generate the entrainment stimulation pulses 802 for a predefined duration of time. In some examples, processing circuitry 40 may be configured to control stimulation generator 44 to generate the desynchronization stimulation pulse(s) 804 with a predetermined number of pulses (e.g., 1, 10, 100, etc.). In another example, processing circuitry 40 may be configured to control stimulation generator 44 to generate the desynchronization stimulation pulse(s) 804 for a predefined duration of time. The duration of time for each phase may be the different, but in some instances, processing circuitry 40 may determine the duration of time to be the same for two or more different phases. In such examples, responsive to generating the predetermined number of pulses of the one or more desynchronization stimulation pulses, processing circuitry 40 may control stimulation generator 44 to generate entrainment stimulation waveform 806 following desynchronization stimulation waveforms 804. In one example, responsive to generating the one or more desynchronization stimulation pulses for the predefined duration of time, processing circuitry 40 may control stimulation generator 44 to generate entrainment stimulation waveform 806 following desynchronization stimulation waveforms 804. Processing circuitry may control stimulation generator 44 to generate entrainment stimulation waveform 806 again for a predefined duration of time. It should be noted that the predefined duration of time for entrainment stimulation waveform 806 may or may not be the same duration of time as defined for entrainment stimulation waveform 802.

Figure 9:
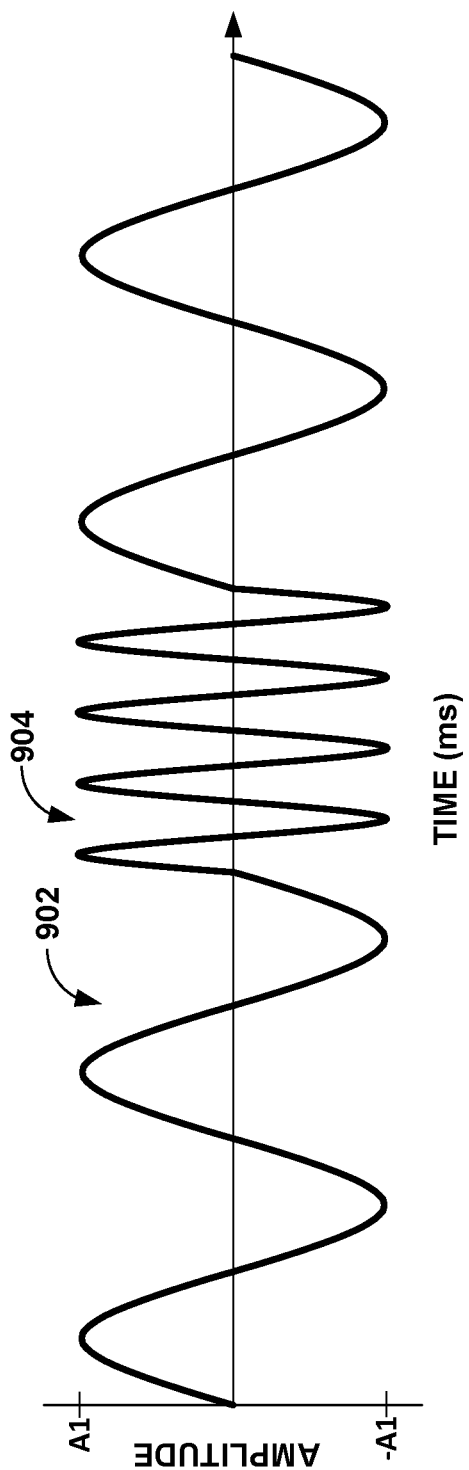
FIG. 9 is a chart illustrating an example electrical stimulation waveform being modulated in accordance with one or more techniques of the disclosure.

FIG. 9 is a chart illustrating an example electrical stimulation waveform modulated to have different frequencies over time. The example of FIG. 9 is similar to FIG. 8 except that the amplitude of the desynchronization stimulation waveforms 904 is the same as the entrainment stimulation waveforms 902, whereas stimulation generator 44 has altered the frequency. In an illustrative example, the frequency may be increased from 80 Hertz to more than 100 Hertz, such as increased to a frequency of 130 Hertz.

Figure 10:
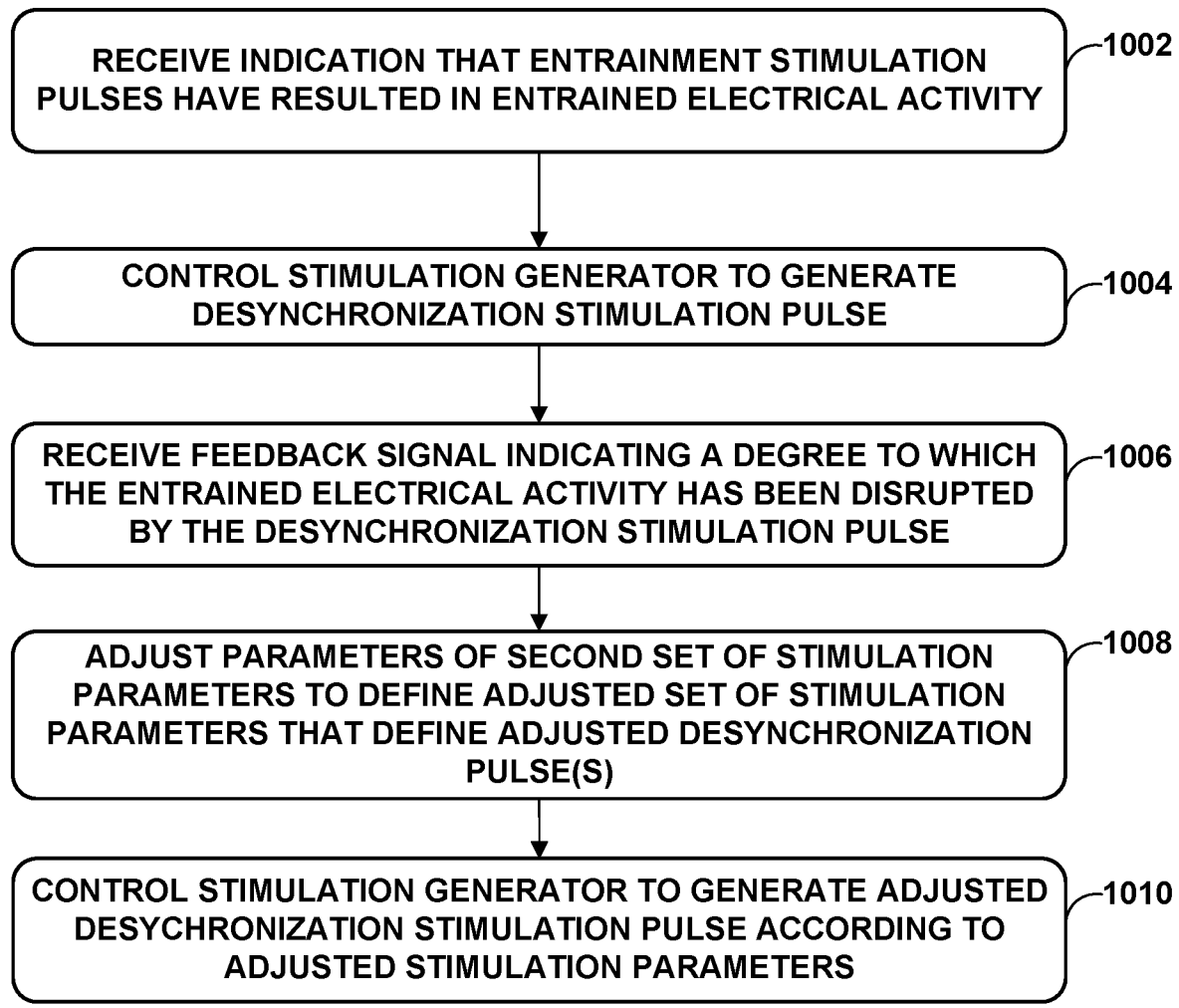
FIG. 10 is a flow diagram illustrating an example operation for delivering electrical stimulation to the brain of a patient by utilizing feedback signals in accordance with one or more techniques of the disclosure.

FIG. 10 is a flow diagram illustrating an example operation for delivering electrical stimulation to brain 28 of patient 12 by utilizing feedback signals. As such, processing circuitry 40 may cause stimulation generator 44 to deliver stimulation pulses in a closed loop configuration. That is, processing circuitry 40 may trigger changes in stimulation pulse phases based on patient feedback, such as based on data received from sensing circuitry 46.

In some examples, processing circuitry 40 may receive an indication that the entrainment stimulation pulses have resulted in entrained electrical activity (1002). For example, processing circuitry 40 may receive an indication that delivery of the entrainment stimulation pulses has resulted in electrical activity of patient 12 being entrained. In one example, one or more biomarkers may indicate that a particular VOA is following an entrained waveform pattern.

In some examples, processing circuitry 40 may control stimulation generator 44 to generate the desynchronization stimulation pulse(s) (1004). For example, responsive to receiving the indication that delivery of the entrainment stimulation pulses has resulted in electrical activity of patient 12 being entrained, processing circuitry 40 may control stimulation generator 44 to generate the set of one or more desynchronization stimulation pulse(s). Processing circuitry 40 may control stimulation generator 44 to generate the set of desynchronization stimulation pulse(s) to one or more of electrodes 24, 26.

In some examples, processing circuitry 40 may receive one or more feedback signals indicating a degree to which the desynchronization stimulation pulse(s) has disrupted at least a portion of the entrained electrical activity (1006). For example, processing circuitry 40 may receive a feedback signal indicating a degree of efficacy of the set of desynchronization stimulation pulse(s) in disrupting the entrained electrical activity. In some examples, the feedback signals may indicate a degree of disruption by indicating a change in biomarkers characteristics. For example, the feedback signals may include signals indicating biomarker characteristics of a particular disease, such as beta in Parkinson's disease (e.g., beta activity, beta oscillations, etc.). In some examples, the feedback signals may include indications of changes in biomarker characteristics. In the illustrative example of a Parkinson's disease treatment, the feedback signals may indicate beta changes indicating improved or beta and/or longer lasting desired beta (e.g., "good" beta). Processing circuitry 40 may utilize such feedback signals to adjust parameters of the desynchronization phase. In a non-limiting example, processing circuitry 40 may shorten the desynchronization phase in response to such feedback signals indicating such improvements in patient 12. In one example, processing circuitry 40 may receive the feedback signals from one of external devices 34, such as from a wearable device. In some examples, the feedback signals may be the same signals used to determine parameters for one or both the entrainment phase and the desynchronization phase. For example, processing circuitry may determine duration parameters for the entrainment pulses and the desynchronization phases based on signals received from one of external devices 34. In such examples, processing circuitry 40 may adjust the duration parameters as treatment progresses based on signals received from the same one of the external devices 34, such as a wearable device configured to identify and track beta biomarker characteristics. It should be noted that the set of desynchronization stimulation pulses may include only one desynchronization stimulation pulse, in some instances, and likewise, the set of desynchronization stimulation pulses may include the at least one desynchronization stimulation pulse as part of the set.

In some examples, processing circuitry 40 may adjust one or more parameters of the second set of stimulation parameters to define an adjusted set of stimulation parameters (1008). The adjusted set of stimulation parameters may define at least one adjusted desynchronization stimulation pulse. In other examples, the adjusted set of stimulation parameters may define adjusted entrainment stimulation pulses.

In some examples, processing circuitry 40 may determine, based at least in part on the feedback signal, an adjusted plurality of stimulation parameters for adjusting the desynchronization stimulation pulse(s). For example, processing circuitry 40 may control stimulation generator 44 to increase or decrease the frequency of the desynchronization stimulation pulse(s), either in a next repeating phase or as part of the currently executing phase. Likewise, processing circuitry 40 may control stimulation generator 44 to increase or decrease the frequency of the entrainment stimulation pulses, either in a next repeating phase or as part of the currently executing phase. In some examples, processing circuitry 40 may control stimulation generator 44 to generate at least one adjusted desynchronization stimulation pulse(s) according to the adjusted set of stimulation parameters (1010). As such, processing circuitry 40 may control stimulation generator 44 to deliver adjusted desynchronization stimulation pulse(s), or adjusted entrainment stimulation pulses, according to the adjusted set of stimulation parameters.

While described with reference to processing circuitry 40 of IMD 16, the techniques of this disclosure are not so limited, and the techniques of this disclosure may be implemented by other processing circuitry (alone or in combination with processing circuitry of another device), such as processing circuitry 60 of programmer 14 or processing circuitry of external device 34 or an external server. For example, processing circuitry 60 may determine adjustments to stimulation parameters and transmit the adjusted stimulation parameters to IMD 16, thereby causing IMD 16 (e.g., stimulation generator 44) to deliver the electrical stimulation pulses. In addition, it will be understood that some techniques of FIG. 10 may be combined or omitted altogether. For example, processing circuitry, such as that of IMD 16, may determine adjusted stimulation parameters that define the desynchronization stimulation pulses prior to the delivery of the first set of desynchronization stimulation pulses to patient 12. In such instances, the first set of desynchronization stimulation pulses may also be based on adjusted stimulation parameters.

Figure 11:
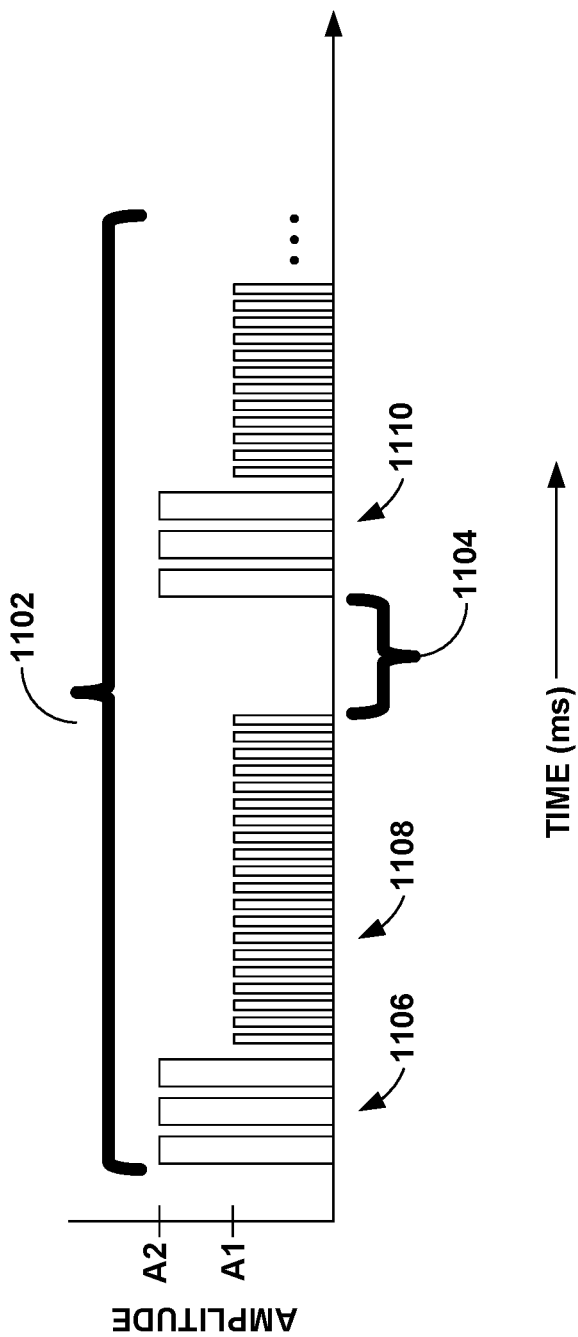
FIG. 11 is a chart illustrating example modulation of electrical stimulation pulses and an example rest phase in accordance with one or more techniques of the disclosure.

FIG. 11 is a chart illustrating example modulation of electrical stimulation pulses 1102. In the example of FIG. 11, the electrical stimulation pulses 1102 include an example rest phase 1104, example entrainment stimulation pulses 1106, 1110, and example desynchronization pulses 1108. In some examples, processing circuitry 40 may control stimulation generator 44 to interleave a rest phase between generation of the entrainment stimulation pulses 1110 and the desynchronization stimulation pulse(s) 1108, as shown. In such examples, a duration of the rest phase may be patient specific. For example, processing circuitry 40 may determine the duration of the rest phase using the following example equation: f_4=d*f_patient, where d is a scaling factor, f_4 is the rest phase duration or in particular instances, the rest phase frequency, and f_patient is the patient specific signal (e.g., physiological signal).

In some examples, processing circuitry 40 may adjust a duration of the rest phase from a first rest phase duration to a second rest phase duration based at least in part on one or more biomarkers of patient 12. For example, processing circuitry 40 may shorten the rest phase duration or lengthen the rest phase duration over time. For example, processing circuitry 40 may adjust the duration of the second rest phase to be shorter than the duration of the first rest phase. That is, processing circuitry 40 may decrease the duration of the rest phase over time, such that a subsequent rest phase has a shorter duration than a preceding rest phase duration. In one illustrative example, processing circuitry 40 may decrease the duration of the rest phase until the rest phase is removed (e.g., the subsequent rest phase has a duration of 0 seconds).

Figure 12:
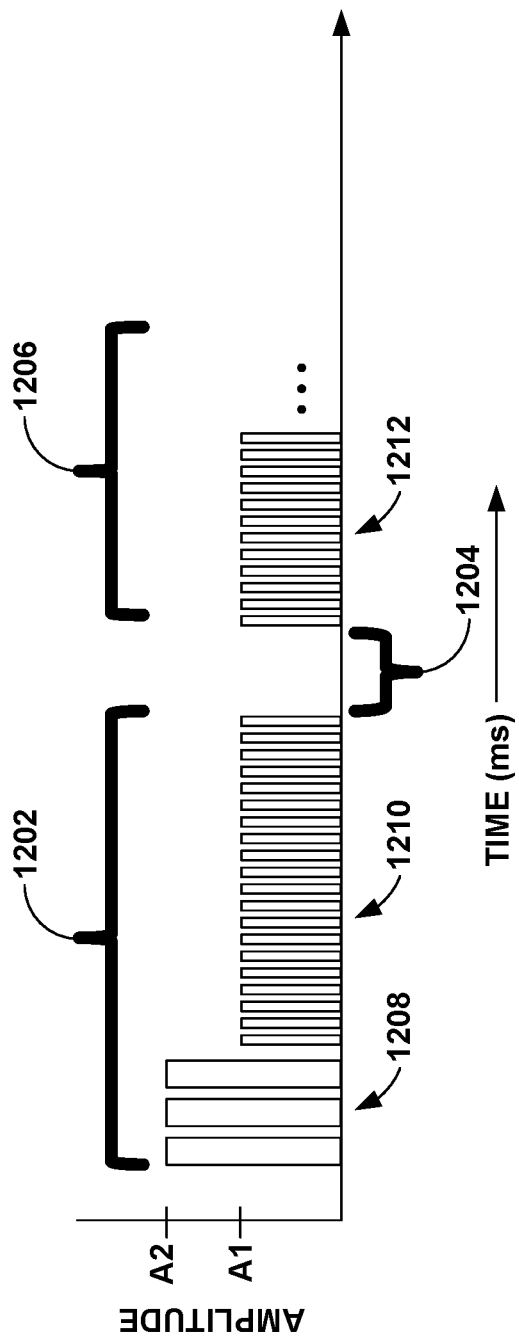
FIG. 12 is a chart illustrating example modulation of electrical stimulation pulses and an example rest phase in accordance with one or more techniques of the disclosure.

FIG. 12 is a chart illustrating example modulation of electrical stimulation pulses 1202 and an example rest phase 1204. Electrical stimulation pulses 1202 may include both entrainment stimulation pulses 1208 and desynchronization stimulation pulses 1210. In the example of FIG. 12, a rest phase is interleaved between desynchronization pulses 1210 from stimulation pulses 1202 and desynchronization pulses 1212 from stimulation pulses 1206. In some examples, a rest phase, such as rest phase 1204, may only be used in the closed loop configuration.

Figure 13:
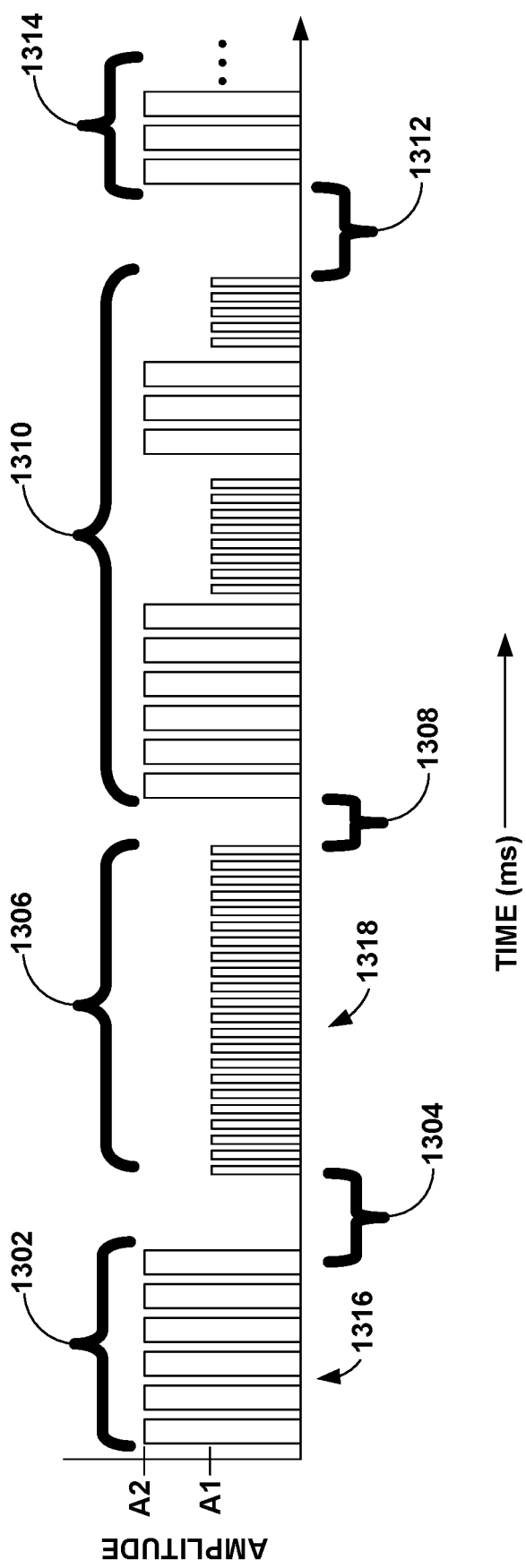
FIG. 13 is a chart illustrating example modulation of electrical stimulation pulses and example rest phases in accordance with one or more techniques of the disclosure.

FIG. 13 is a chart illustrating example modulation of electrical stimulation pulses 1302, 1306, 1310, 1314 and example rest phases 1304, 1308, 1312. In such examples, inter-pulse periods of rest or transition pulses can be interleaved between delivery of entrainment stimulation pulses and the desynchronization stimulation pulse(s). The rest phases 1304, 1308, 1312 may be included in order to allow for the natural evolution of network population resynchronization to occur. Since patient symptoms may not be present before resynchronization occurs, the system may withhold stimulation during the rest phases 1304, 1308, 1312 in order to conserve power when stimulation is not necessary to treat the patient. As shown, in some examples, electrical stimulation pulses 1302 may include entrainment stimulation pulses 1316, desynchronization stimulation pulses 1318, or both, as in the example electrical stimulation pulses 1310.

Figure 14:
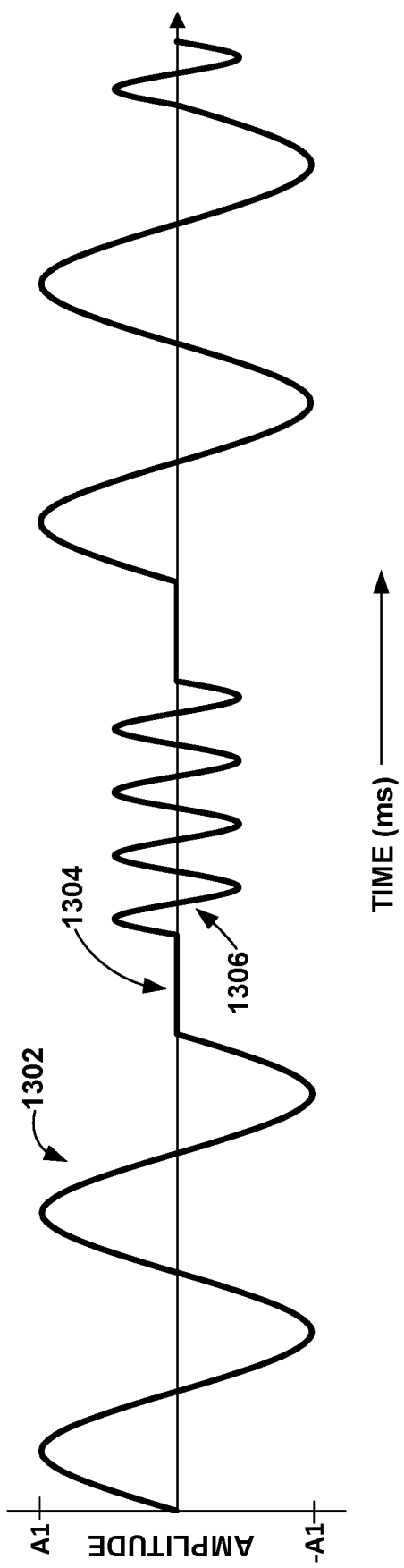
FIG. 14 is a chart illustrating an example electrical stimulation waveform including rest phases and being modulated in accordance with one or more techniques of the disclosure.

FIG. 14 is a chart illustrating an example electrical stimulation waveform including rest phases 1304. The electrical stimulation waveform includes entrainment stimulation pulses 1302 and desynchronization stimulation pulses 1306 in the form of waveforms. In the example of FIG. 14, the entrainment stimulation pulses 1302 and desynchronization stimulation pulses 1306 are separated by a rest phase 1304. As in FIG. 8 or 9, the amplitude of FIG. 14 may be in units of V or mA depending on the configuration of the electrical stimulation therapy, and the time axis may be in units of milliseconds.

In some examples, processing circuitry 40 may cause stimulation generator 44 to deliver the entrainment stimulation pulses and the at least one desynchronization stimulation pulse in an open loop configuration. In addition, processing circuitry 40 may progress to delivering the entrainment stimulation pulses and the desynchronization stimulation pulse(s) in a closed loop configuration involving feedback from the electrical stimulation system. In such examples, the closed loop configuration may have one or more rest phases interleaved between the entrainment stimulation pulses and the desynchronization stimulation pulse(s).

Processing circuitry 40 may then determine a degree of synchrony obtained in a neuronal subpopulation of the brain. For example, Processing circuitry 40 may determine the degree of synchrony during a first rest phase. In addition, during delivery of the entrainment stimulation pulses and the at least one desynchronization stimulation pulse in the closed loop configuration, processing circuitry 40 may determine a duration for the second rest phase different from the first rest phase based on one or more biomarkers of patient 12. For example, processing circuitry may determine the duration for the second rest phase based at least in part on the degree of network synchrony obtained from prior stimulation pulses.

For example, the open loop configuration may or may not have a rest phase. The open loop configuration may then progress to form a closed loop. In the closed loop configuration, processing circuitry 40 may cause stimulation generator to introduce a rest phase, in cases where the open loop configuration did not have a rest phase, or in some cases, continue providing a rest phase, such as by causing stimulation generator 44 to cease delivering stimulation. The rest phase duration may be based on one or more biomarkers. The rest phase may increase in duration when the target neural network is in synchrony or is behaving according to an expected behavior determined based on the desynchronization and/or entrainment stimulation pulses. If the network starts misbehaving, however, then processing circuitry 40 may shorten the duration of the rest phase, such as by removing the rest phase altogether.

Figure 15:
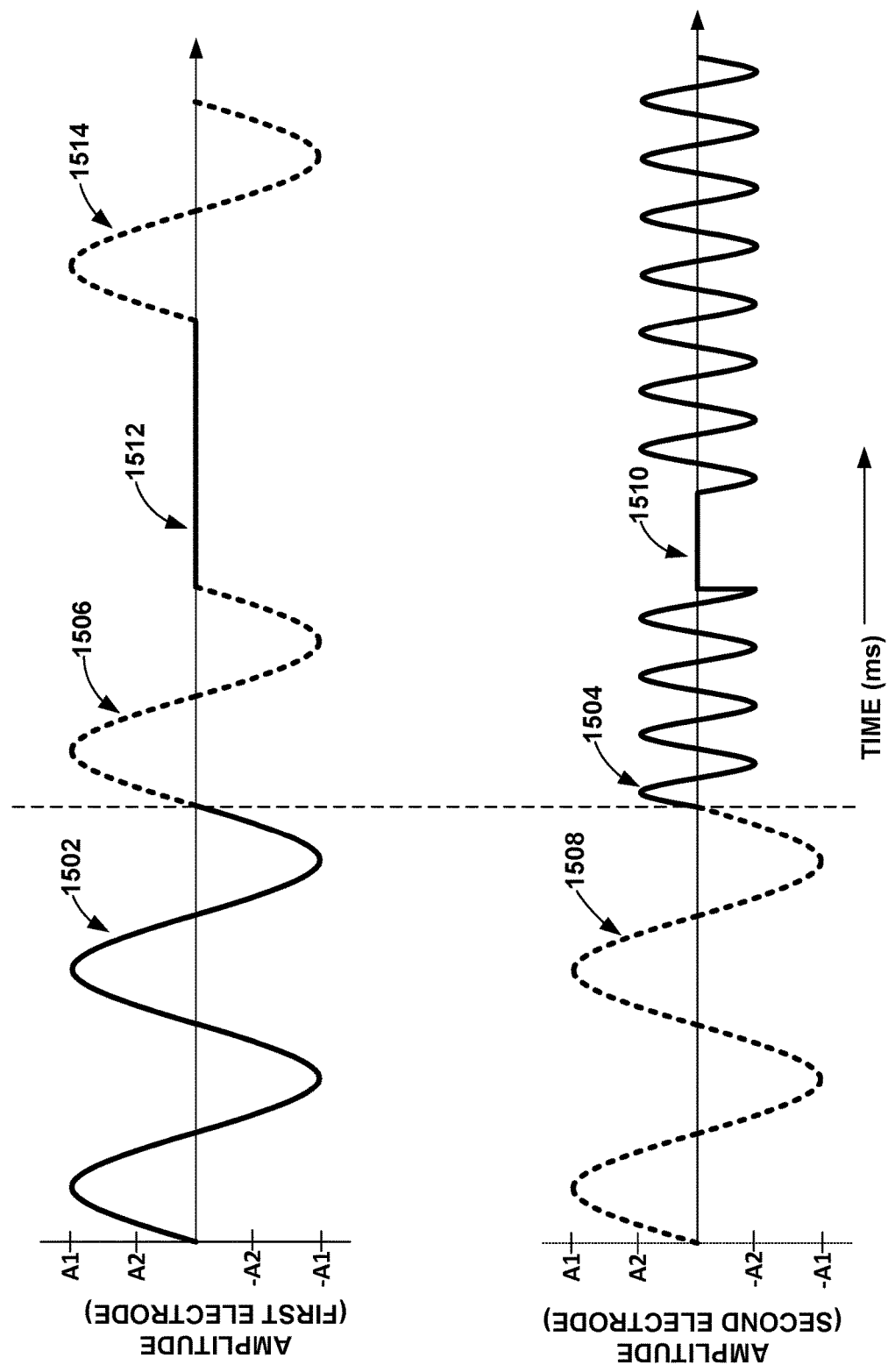
FIG. 15 is a chart illustrating example electrical stimulation waveforms being delivered to multiple electrodes in accordance with one or more techniques of the disclosure.

FIG. 15 is a chart illustrating example electrical stimulation waveforms being delivered to multiple electrodes. The dashed lines indicate optional delivery of pulses. The stimulation includes entrainment stimulation pulses 1502, 1508, and optionally 1506. The stimulation also includes rest phases 1512 and 1510. The stimulation also includes desynchronization stimulation pulses 1504. In such examples, the desynchronization stimulation pulses 1504 may be delivered at substantially the same time as entrainment stimulation pulses 1506. As in FIG. 8, 9, or 14, the amplitude of FIG. 15 may be in units of V or mA depending on the configuration of the electrical stimulation therapy, and the time axis may be in units of milliseconds.

In another example, processing circuitry 40 may determine a source of pathology in brain 28 of patient 12 in order to determine the stimulation parameters that define the desynchronization stimulation pulse(s). For example, processing circuitry 40 may receive physiological signals or biomarkers indicating the pathology source. As such, processing circuitry 40 may determine the source of pathology in brain 28 of patient 12. In such examples, processing circuitry 40 may also identify a neuronal subpopulation of brain 28 of patient 12 relating to the source of the pathology. As such, processing circuitry 40 may determine the stimulation parameters that define the desynchronization stimulation pulse(s) based at least in part on the identified neuronal subpopulation relating to the source of the pathology. In particular, processing circuitry 40 may determine the stimulation parameters so as to target the neuronal subpopulation using the desynchronization stimulation pulse(s).

In some examples, processing circuitry 40 may determine a change in pathology of a patient. In such examples, processing circuitry 40 may alter a directionality of the at least one desynchronization stimulation pulse from targeting a first subpopulation to targeting a second subpopulation based at least in part on the determined change in pathology.

Regardless of how the pathological brain signals are identified, by disrupting the oscillations of the bioelectrical brain signals using desynchronization stimulation pulses within one or more pathological frequency regions, motor symptoms that manifest themselves when certain frequency oscillations are present may be reduced or substantially eliminated using the various examples of this disclosure.

The techniques described in this disclosure may be implemented, at least in part, in hardware, software, firmware or any combination thereof. For example, various aspects of the described techniques may be implemented within one or more processors or processing circuitry, including one or more microprocessors, DSPs, ASICs, FPGAs, or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit including hardware may also perform one or more of the techniques of this disclosure.

Such hardware, software, and firmware may be implemented within the same device or within separate devices to support the various operations and functions described in this disclosure. In addition, any of the described units, circuits or components may be implemented together or separately as discrete but interoperable logic devices. Depiction of different features as circuits or units is intended to highlight different functional aspects and does not necessarily imply that such circuits or units must be realized by separate hardware or software components. Rather, functionality associated with one or more circuits or units may be performed by separate hardware or software components or integrated within common or separate hardware or software components.

The techniques described in this disclosure may also be embodied or encoded in a computer-readable medium, such as a computer-readable storage medium, containing instructions that may be described as non-transitory media. Instructions embedded or encoded in a computer-readable storage medium may cause a programmable processor, or other processor, to perform the method, e.g., when the instructions are executed. Computer readable storage media may include RAM, ROM, PROM, EPROM, EEPROM, flash memory, a hard disk, a CD-ROM, a floppy disk, a cassette, magnetic media, optical media, or other computer readable media.

In addition, it should be noted that the systems described herein may not be limited to treatment of a human patient. In alternative examples, these systems may be implemented in non-human patients, e.g., primates, canines, equines, pigs, and felines. These animals may undergo clinical or research therapies that my benefit from the subject matter of this disclosure.

Various examples of the disclosure have been described. These and other examples are within the scope of the following claims.

What is claimed is:

1. A system comprising:
  a stimulation generator configured to generate stimulation pulses deliverable via at least one electrical lead comprising at least one electrode; and
  processing circuitry configured to:
    determine a first set of stimulation parameters that define entrainment stimulation pulses configured to entrain electrical activity in a brain of a patient;
    control the stimulation generator to generate the entrainment stimulation pulses according to the first set of stimulation parameters;
    determine a second set of stimulation parameters that define at least one desynchronization stimulation pulse configured to disrupt at least a portion of electrical activity of the brain entrained by the entrainment stimulation pulses, the second set of stimulation parameters being different from the first set of stimulation parameters; and
    subsequent to generating the entrainment stimulation pulses, control the stimulation generator to generate the at least one desynchronization stimulation pulse according to the second set of stimulation parameters.

2. The system of claim 1, wherein to determine the second set of stimulation parameters, the processing circuitry is further configured to:
  obtain a physiological signal from the patient;
  identify one or more biomarkers from the physiological signal and for the patient; and
  determine the second set of stimulation parameters based at least in part on the one or more biomarkers for the patient.

3. The system of claim 2, further comprising a housing configured to contain the stimulation generator and the processing circuitry, wherein to identify the one or more biomarkers for the patient, the processing circuitry is further configured to:
  receive the physiological signal from a sensing device external to and distinct from the housing, the sensing device configured to detect the physiological signal from the patient.

4. The system of claim 2, wherein the physiological signal comprises a local field potential (LFP) signal originating from within one or more regions of the brain, and wherein to identify the one or more biomarkers for the patient, the processing circuitry is further configured to:
  identify the one or more biomarkers from the LFP, the one or more biomarkers configured to indicate a neural state of the patient.

5. The system of claim 4, wherein the one or more biomarkers comprise a frequency between approximately 0.1 Hertz (Hz) and 500 Hz.

6. The system of claim 1, wherein the first set of stimulation parameters are configured to entrain electrical activity of a first region of the brain, and wherein the second set of stimulation parameters are configured to cause destructive interference for entrained electrical activity within a second region of the brain smaller than the first region of the brain.

7. The system of claim 1, wherein the at least one electrode comprises a first electrode combination, wherein the processing circuitry is further configured to:
  cause the stimulation generator to deliver the entrainment stimulation pulses to the first electrode combination;
  determine that the entrainment stimulation pulses have resulted in electrical activity being entrained in the patient; and
  responsive to determining that the entrainment stimulation pulses have resulted in electrical activity being entrained in the patient, cause the stimulation generator to deliver the at least one desynchronization stimulation pulse to a second electrode combination different than the first electrode combination.

8. The system of claim 1,
  wherein the first set of stimulation parameters includes a first pulse frequency below approximately 100 Hz, and
  wherein the second set of stimulation parameters includes a second pulse frequency between approximately 30 Hz and 125 Hz higher than the first pulse frequency.

9. The system of claim 1, wherein the at least one desynchronization stimulation pulse comprises a plurality of desynchronization stimulation pulses, and wherein the processing circuitry is further configured to:
  control the stimulation generator to generate the entrainment stimulation pulses for a first predefined duration of time;
  control the stimulation generator to generate the plurality of desynchronization stimulation pulses for a second predefined duration of time; and
  responsive to generating the plurality of desynchronization stimulation pulses for the second predefined duration of time, control the stimulation generator to generate the entrainment stimulation pulses again for the first predefined duration of time.

10. The system of claim 1, wherein the processing circuitry is further configured to:
  receive an indication that the entrainment stimulation pulses have resulted in electrical activity of the patient being entrained;
  responsive to receiving the indication, control the stimulation generator to generate a set of desynchronization stimulation pulses;
  receive a feedback signal indicating a degree of efficacy of the set of desynchronization stimulation pulses in disrupting the entrained electrical activity;
  adjusting, based at least in part on the feedback signal, one or more parameters of the second set of stimulation parameters to define an adjusted set of stimulation parameters that define at least one adjusted set of desynchronization stimulation pulses; and
  control the stimulation generator to generate the at least one adjusted set of desynchronization stimulation pulse according to the adjusted set of stimulation parameters.

11. The system of claim 1, wherein the processing circuitry is further configured to:
  control the stimulation generator to interleave a rest phase between generation of the entrainment stimulation pulses and the at least one desynchronization stimulation pulse, wherein the processing circuitry is configured to withhold electrical stimulation during the rest phase.

12. The system of claim 1, further comprising an implantable medical device (IMD) that comprises the stimulation generator and the processing circuitry.

13. A method comprising:
  determining a first set of stimulation parameters that define entrainment stimulation pulses configured to entrain electrical activity in a brain of a patient;
  controlling a stimulation generator to generate the entrainment stimulation pulses according to the first set of stimulation parameters;
  determining a second set of stimulation parameters that define at least one desynchronization stimulation pulse configured to disrupt at least a portion of electrical activity of the brain entrained by the entrainment stimulation pulses, the second set of stimulation parameters being different from the first set of stimulation parameters; and
  subsequent to generating the entrainment stimulation pulses, controlling the stimulation generator to generate the at least one desynchronization stimulation pulse according to the second set of stimulation parameters.

14. The method of claim 13, wherein determining the second set of stimulation parameters comprises:
  obtaining a physiological signal from the patient;
  identifying one or more biomarkers from the physiological signal and for the patient; and
  determining the second set of stimulation parameters based at least in part on the one or more biomarkers for the patient.

15. The method of claim 13, wherein the first set of stimulation parameters are configured to entrain electrical activity of a first region of the brain, and wherein the second set of stimulation parameters are configured to cause destructive interference for entrained electrical activity within a second region of the brain smaller than the first region of the brain.

16. The method of claim 13, further comprising:
causing the stimulation generator to deliver the entrainment stimulation pulses to a first electrode combination;
determining that the entrainment stimulation pulses have resulted in electrical activity being entrained in the patient; and
responsive to determining that the entrainment stimulation pulses have resulted in electrical activity being entrained in the patient, causing the stimulation generator to deliver the at least one desynchronization stimulation pulse to a second electrode combination different than the first electrode combination.

17. The method of claim 13,
wherein the first set of stimulation parameters includes a first pulse frequency below approximately 100 Hz, and
wherein the second set of stimulation parameters includes a second pulse frequency between approximately 30 Hz and 125 Hz higher than the first pulse frequency.

18. A non-transitory computer-readable storage medium having stored thereon instructions that, when executed, cause one or more processors to:
determine a first set of stimulation parameters that define entrainment stimulation pulses configured to entrain electrical activity in a brain of a patient;
control a stimulation generator to generate the entrainment stimulation pulses according to the first set of stimulation parameters;
determine a second set of stimulation parameters that define at least one desynchronization stimulation pulse configured to disrupt at least a portion of electrical activity of the brain entrained by the entrainment stimulation pulses, the second set of stimulation parameters being different from the first set of stimulation parameters; and
subsequent to generating the entrainment stimulation pulses, control the stimulation generator to generate the at least one desynchronization stimulation pulse according to the second set of stimulation parameters.

19. The system of claim 1, wherein the first set of stimulation parameters comprises a first amplitude, wherein the second set of stimulation parameters comprises a second amplitude, and wherein the second amplitude is higher than the first amplitude.

20. The system of claim 1, wherein the entrainment stimulation pulses comprise a first set of entrainment stimulation pulses, wherein the at least one desynchronization stimulation pulse comprises a first set of desynchronization pulses, and wherein the processing circuitry is configured to:
control the stimulation generator to generate and deliver a second set of entrainment stimulation pulses after the first set of desynchronization pulses are delivered; and
control the stimulation generator to generate and deliver a second set of desynchronization pulses after the second set of entraining stimulation pulses are delivered, wherein at least one of: the second set of entrainment stimulation pulses comprises fewer entrainment stimulation pulses than the first set of entrainment stimulation pulses, or the second set of desynchronization pulses comprises fewer desynchronization stimulation pulses than the first set of desynchronization stimulation pulses.

21. The method of claim 13, wherein the first set of stimulation parameters comprises a first amplitude, wherein the second set of stimulation parameters comprises a second amplitude, and wherein the second amplitude is higher than the first amplitude.

22. The method of claim 13, wherein the entrainment stimulation pulses comprise a first set of entrainment stimulation pulses, wherein the at least one desynchronization stimulation pulse comprises a first set of desynchronization pulses, and wherein the method further comprises:
controlling the stimulation generator to generate and deliver a second set of entrainment stimulation pulses after the first set of desynchronization pulses are delivered; and
controlling the stimulation generator to generate and deliver a second set of desynchronization pulses after the second set of entraining stimulation pulses are delivered, wherein at least one of: the second set of entrainment stimulation pulses comprises fewer entrainment stimulation pulses than the first set of entrainment stimulation pulses, or the second set of desynchronization pulses comprises fewer desynchronization stimulation pulses than the first set of desynchronization stimulation pulses.

* * * * *